United States Patent
Feng et al.

(10) Patent No.: US 11,155,632 B2
(45) Date of Patent: Oct. 26, 2021

(54) ANTI-CD47 MONOCLONAL ANTIBODY AND USE THEREOF

(71) Applicant: CHANGCHUN GENESCIENCE PHARMACEUTICAL CO., LTD., Jilin (CN)

(72) Inventors: Xiao Feng, Jilin (CN); Lei Jin, Jilin (CN); Liang Xiao, Jilin (CN); Tao Wang, Jilin (CN); Suofu Qin, Jilin (CN)

(73) Assignee: CHANGCHUN GENESCIENCE PHARMACEUTICAL CO., LTD., Jilin (CN)

( * ) Notice: Subject to any disclaimer, the term of this patent is extended or adjusted under 35 U.S.C. 154(b) by 0 days.

(21) Appl. No.: 16/310,748

(22) PCT Filed: Jun. 13, 2017

(86) PCT No.: PCT/CN2017/088013
§ 371 (c)(1),
(2) Date: Dec. 17, 2018

(87) PCT Pub. No.: WO2017/215585
PCT Pub. Date: Dec. 21, 2017

(65) Prior Publication Data
US 2020/0079869 A1    Mar. 12, 2020

(30) Foreign Application Priority Data

Jun. 17, 2016 (CN) .......................... 201610436519.3

(51) Int. Cl.
| | | |
|---|---|---|
| *A61K 39/395* | (2006.01) | |
| *A61K 39/00* | (2006.01) | |
| *C07K 16/28* | (2006.01) | |
| *C07K 14/705* | (2006.01) | |
| *C07K 16/30* | (2006.01) | |
| *C12N 5/16* | (2006.01) | |
| *G01N 33/574* | (2006.01) | |
| *G01N 33/577* | (2006.01) | |
| *G01N 33/68* | (2006.01) | |
| *A61K 38/00* | (2006.01) | |

(52) U.S. Cl.
CPC .... *C07K 16/2896* (2013.01); *C07K 14/70503* (2013.01); *C07K 16/2803* (2013.01); *C07K 16/3061* (2013.01); *C12N 5/163* (2013.01); *G01N 33/574* (2013.01); *G01N 33/577* (2013.01); *G01N 33/68* (2013.01); *A61K 38/00* (2013.01); *A61K 2039/505* (2013.01); *C07K 2317/56* (2013.01); *C07K 2317/73* (2013.01); *C07K 2317/76* (2013.01); *C07K 2317/92* (2013.01); *C12N 2510/02* (2013.01); *G01N 2333/70596* (2013.01)

(58) Field of Classification Search
CPC .................................................. C07K 16/2896
See application file for complete search history.

(56) References Cited

U.S. PATENT DOCUMENTS

| | | | |
|---|---|---|---|
| 9,221,908 B2 | 12/2015 | Frazier et al. | |
| 2014/0140989 A1* | 5/2014 | Eckelman | C07K 16/2803 424/133.1 |

FOREIGN PATENT DOCUMENTS

| | | |
|---|---|---|
| CN | 104271757 | 1/2015 |
| CN | 105101997 | 11/2015 |
| CN | 106084052 | 11/2016 |
| WO | WO 2010/104749 A2 * | 9/2010 |
| WO | WO 2015/191861 | 12/2015 |
| WO | WO 2016/081423 | 5/2016 |

OTHER PUBLICATIONS

Bedzyk et al., The Journal of Biological Chemistry, 1990; 265(1): 133-138 (Year: 1990).*
Paul, William E., Fundamental Immunology, 3rd Edition, Raven Press, New York, Chap. 8, pp. 292-295 (1993) (Year: 1993).*
Rudikoff et al., Proc. Natl. Acad. Sci. USA, 79(6):1979-1983, Mar. 1982 (Year: 1982).*
Colman P. M., Research in Immunology, 145:33-36, 1994 (Year: 1994).*
Bendig M. M., Methods: A Companion to Methods in Enzymology, 1995; 8:83-93 (Year: 1995).*
MacCallum et al., J. Mol. Biol., 262, 732-745, 1996 (Year: 1996).*
Casset et al., Biochemical and Biophysical Research Communications, 307:198-205, 2003 (Year: 2003).*

* cited by examiner

*Primary Examiner* — Gary B Nickol
*Assistant Examiner* — Lakia J Jackson-Tongue
(74) *Attorney, Agent, or Firm* — IP & T Group LLP

(57) ABSTRACT

An anti-CD47 monoclonal antibody and use thereof. The provided anti-CD47 monoclonal antibody can effectively inhibit tumor growth. Blocking human SIRP and human CD47 signals may enhance macrophage phagocytosis of tumor cells, prevent the tumor cells from escaping a tumor immune defense system, and have an anti-tumor function. Blocking association between the CD47 on a tumor cell surface and the SIRP on a macrophage surface may block a "do not eat me" signal from the tumor cells, promoting tumor cell recognition and uptake of macrophages, and thereby facilitating tumor cells to be phagocytosed. The association between the CD47 on a tumor cell surface and the SIRP on a macrophage surface is a common "do not eat me" signal. The anti-CD47 antibody, as a very promising target in the tumor immune system, will play a powerful and effective role in human cancer therapy.

11 Claims, 5 Drawing Sheets
Specification includes a Sequence Listing.

ANTI-CD47 MONOCLONAL ANTIBODY AND USE THEREOF

The present application is a national stage application of PCT/CN2017/088013 filed on Jun. 13, 2017, which claims priority to Chinese patent application No. 201610436519.3 filed with the Chinese Patent Office (SIPO) on Jun. 17, 2016, entitled "An anti-CD47 monoclonal antibody and use thereof". The disclosure of each of the forgoing applications is incorporated herein by reference in its entirety.

TECHNICAL FIELD

The present invention relates to the technical field of antibody drugs, specifically, to an anti-CD47 monoclonal antibody and use thereof.

BACKGROUND ART

CD47

CD47, also known as integrin-associated protein (IAP), was originally found from co-purification of human placenta and integrin aV$\beta_3$ and co-immunoprecipitation of platelets and $\beta_3$ integrin. It is a transmembrane glycoprotein widely expressed on cell surface, and belongs to the immunoglobulin superfamily.

CD47 is a crucial marker on cell surface, with a molecular weight between 47 kD and 55 kD. It structurally includes an amino-terminal extracellular variable region, a transmembrane region composed of 3 to 5 highly hydrophobic transmembrane segments and a hydrophilic carboxy-terminal cytoplasmic tail. It interacts with a variety of ligands such as integrins, SIRPα (signal regulatory protein α), SIRPγ, and thrombospondin.

SIRPα

Signal regulatory protein α (SIRPα) is also a transmembrane protein expressed primarily on the surface of macrophages, dendritic cells and nerve cells. Its extracellular domain contains three immunoglobulins superfamily-like regions in which the N-terminal region mediates the binding to CD47 and its intracellular domain has a typical immunoreceptor tyrosine inhibitory sequence (ITIM). Upon binding to CD47, ITIM of SIRPα is phosphorylated, and a cascade reaction occurs, and the phagocytosis of macrophages is inhibited.

CD47/SIRPα is Involved in the Mechanism of Tumor Immune Escape

In the innate immune system, CD47, as a marker of self, functions by transmitting an inhibitory "do not eat me" signal through binding with SIRPα expressed by myeloid cells such as macrophages, neutrophils, and dendritic cells. Thus, the broad expression of CD47 under physiological conditions is to protect healthy cells from being eliminated by the innate immune system. However, tumor cells effectively escape immune surveillance by overexpressing CD47.

In recent years, the CD47 and CD47-SIRPα signaling systems have received extensive attention. Among them, the most remarkable thing is that it is a potential drug target for cancer treatment. Studies have confirmed that CD47 expression is upregulated in most human cancers (eg, NHL, AML, breast cancer, colon cancer, glioblastoma, glioma, ovarian cancer, bladder cancer, and prostate cancer), and the elevated level of CD47 expression is associated with invasive diseases and poor survival. Weissman of the Stanford University systematically studied the expression level of CD47 in various solid tumors. The results indicated that all human solid tumor cells showed high expression of CD47, and the average expression level was about 3.3 times higher than that of normal cells. Moreover, they found that the level of CD47 mRNA in patients with solid tumors was negatively correlated with the prognostic index.

Further experiments on xenograft animal models of in situ immunodeficient mouse have found that administration of anti-CD47 monoclonal antibodies can inhibit the growth and metastasis of large tumors, and can cure small tumors. Willingham et al. also demonstrated the efficacy and safety of anti-CD47 monoclonal antibodies in an experiment with a mouse model of in situ breast cancer. This study not only confirmed that high expression of CD47 is a common mechanism for tumor cells to evade immune surveillance, but also provided valuable reference for the treatment of tumors by blocking CD47-SIRPα signaling pathway.

Therapeutic Anti-CD47 Antibody

CD47 is highly expressed in many types of tumors and acts as a "do not eat me" signal to inhibit phagocytosis, which means that targeting the CD47-SIRPα pathway can be used as a therapeutic method for many types of tumors.

Through in vitro and in vivo experiments, RAUH et al. demonstrated that anti-CD47 blocking monoclonal antibody can promote macrophage phagocytosis of tumor cells, inhibit the formation of acute myeloid leukemia (AML) in mice, and eliminate AML that has been successfully transplanted in vivo. It can also perform targeted elimination of leukemia stem cells (LSC). Study of CHAO et al. on acute lymphoblastic leukemia has found that anti-CD47 monoclonal antibody combined with rituximab can not only eliminate tumors in the original transplant site, but also eliminate tumors in blood circulation and tumors that spread to the liver, spleen, lymph nodes, etc., thereby achieving the effects of long-term survival and inhibition of tumor recurrence, while the use of anti-CD47 monoclonal antibody or anti-CD20 monoclonal antibody alone can only inhibit the growth rate of NHL but cannot completely eliminate NHL.

In order to further confirm the effect of anti-CD47 monoclonal antibody on tumors, WILLINGHAM et al. establishes a xenograft tumor model using immunocompetent mouse. It was confirmed that anti-mouse and anti-human CD47 monoclonal antibodies both significantly inhibit tumor growth and anti-CD47 antibodies can eliminate a variety of solid tumors and inhibit tumor metastasis and recurrence. In addition, anti-CD47 monoclonal antibody also has an anti-tumor effect on cancer stem cells (CSC) and its differentiated subtypes, and can transform tumorigenic TAM into anti-tumor effector factors and enhance their phagocytosis. Inhibition of CD47 expression of mouse can also enhance the sensitivity of tumor cells to radiotherapy, while it has a protective effect on normal tissues, which may be associated with the induction of protective autophagy in host immune cells.

Treatment of tumors with anti-CD47 monoclonal antibodies is associated with a variety of mechanisms. First, anti-CD47 monoclonal antibodies block the binding of the CD47 on a tumor cell to SIRPα on a macrophage and thereby make tumor cells to be phagocytosed. Second, with respect to antibody-dependent and cell-mediated cytotoxicity and complement-dependent cytotoxicity, studies have found that anti-CD47 antibodies can induce cytotoxicity against head and neck tumor cells in which NK cells are involved. Third, tumor cells are eliminated by direct induction of apoptosis. Finally, studies on immunocompetent mice revealed that anti-CD47 monoclonal antibodies can activate CD8[+] T cells, induce acquired T cell immune responses, and further kill tumor cells.

With the deepening of research on the tumor developing molecular mechanism, immunotherapy has gradually become another effective treatment means in addition to the treatments such as surgery and chemical drugs. At present, the role of biotherapy in the treatment of tumors has been increasing year by year. Biotherapy has many advantages in preventing tumor recurrence, treating advanced cancer and its complications. Therefore, there is a need for antibodies and treatments that are capable of targeting CD47.

SUMMARY OF THE INVENTION

In view of the above, the technical problem to be solved by the present invention is to provide an anti-CD47 monoclonal antibody and use thereof. The anti-CD47 monoclonal antibody provided by the present invention can bind human CD47 and monkey CD47, and can block the binding between human SIRP and human CD47 in a dose-dependent manner, and thus promote macrophage phagocytosis of tumor cells. By blocking the binding signal between SIRP and human CD47, tumor cells are prevented from escaping a tumor immune defense system, thus achieving an anti-tumor effect.

The anti-CD47 monoclonal antibody provided by the present invention has a heavy chain variable region and a light chain variable region:

(I) the amino acid sequence of the heavy chain variable region is represented by SEQ ID NO: 1 or SEQ ID NO: 2 or SEQ ID NO: 3 or SEQ ID NO: 4 or SEQ ID NO: 5 or SEQ ID NO: 6 or SEQ ID NO: 7;

(II) the amino acid sequence of the light chain variable region is represented by SEQ ID NO: 8 or SEQ ID NO: 9 or SEQ ID NO: 10 or SEQ ID NO: 11 or SEQ ID NO: 12 or SEQ ID NO: 13 or SEQ ID NO: 14;

(III) an amino acid sequence obtained by substituting or deleting one or more amino acids of the amino acid sequence represented by (I) or (II) or by adding one or more amino acids to the amino acid sequence represented by (I) or (II), and having the same or similar function as the amino acid sequence represented by (I) or (II); or (IV) an amino acid sequence having at least 80% homology to the sequence represented by (I) or (II).

In some specific embodiments of the present invention, in an amino acid sequence obtained by substituting or deleting one or more amino acids of the amino acid sequence of the anti-CD47 monoclonal antibody or by adding one or more amino acids to the amino acid sequence of the anti-CD47 monoclonal antibody, the more amino acids are two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one or thirty-two amino acids.

The substitution occurs in a hypervariable region;

the hypervariable regions of the heavy chain variable region are HVR-H1, HVR-H2, and HVR-H3;

in SEQ ID NO: 2, the hypervariable region HVR-H1 sequence is represented by SEQ ID NO: 45; the HVR-H2 sequence is represented by SEQ ID NO: 46; and the HVR-H3 sequence is represented by SEQ ID NO: 47;

in SEQ ID NO: 5, the hypervariable region HVR-H1 sequence is represented by SEQ ID NO: 48; the HVR-H2 sequence is represented by SEQ ID NO: 49; and the HVR-H3 sequence is represented by SEQ ID NO: 50; and in SEQ ID NO: 6, the hypervariable region HVR-H1 sequence is represented by SEQ ID NO: 51; the HVR-H2 sequence is represented by SEQ ID NO: 52; and the HVR-H3 sequence is represented by SEQ ID NO: 53;

the hypervariable regions of the light chain variable region are HVR-L1, HVR-L2, and HVR-L3;

in SEQ ID NO: 9, the hypervariable region HVR-L1 sequence is represented by SEQ ID NO: 54; the HVR-L2 sequence is represented by SEQ ID NO: 55; and the HVR-L3 sequence is represented by SEQ ID NO: 56;

in SEQ ID NO: 12, the hypervariable region HVR-L1 sequence of is represented by SEQ ID NO: 57; the HVR-L2 sequence is represented by SEQ ID NO: 58; and the HVR-L3 sequence is represented by SEQ ID NO: 59; and in SEQ ID NO: 13, the hypervariable region HVR-L1 sequence is represented by SEQ ID NO: 60; the HVR-L2 sequence is represented by SEQ ID NO: 61; and the HVR-L3 sequence is represented by SEQ ID NO: 62.

The amino acid sequence of the heavy chain variable region is represented by any one of SEQ ID NOs: 1 to 7;

The amino acid sequence of the light chain variable region is represented by any one of SEQ ID NOs: 8 to 14.

In some specific embodiments of the present invention, the anti-CD47 monoclonal antibody comprises:

(i) a heavy chain variable region with an amino acid sequence represented by SEQ ID NOs: 1, 2, 3, 4, 5, 6, or 7, and a light chain variable region with an amino acid sequence represented by SEQ ID NO: 8;

(ii) a heavy chain variable region with an amino acid sequence represented by SEQ ID NOs: 1, 2, 3, 4, 5, 6, or 7, and a light chain variable region with an amino acid sequence represented by SEQ ID NO: 9;

(iii) a heavy chain variable region with an amino acid sequence represented by SEQ ID NOs: 1, 2, 3, 4, 5, 6, or 7, and a light chain variable region with an amino acid sequence represented by SEQ ID NO: 10;

(iv) a heavy chain variable region with an amino acid sequence represented by SEQ ID NOs: 1, 2, 3, 4, 5, 6, or 7, and a light chain variable region with an amino acid sequence represented by SEQ ID NO: 11;

(V) a heavy chain variable region with an amino acid sequence represented by SEQ ID NOs: 1, 2, 3, 4, 5, 6, or 7, and a light chain variable region with an amino acid sequence represented by SEQ ID NO: 12;

(VI) a heavy chain variable region with an amino acid sequence represented by SEQ ID NOs: 1, 2, 3, 4, 5, 6, or 7, and a light chain variable region with an amino acid sequence represented by SEQ ID NO: 13; and (VII) a heavy chain variable region with an amino acid sequence represented by SEQ ID NOs: 1, 2, 3, 4, 5, 6, or 7, and a light chain variable region with an amino acid sequence represented by SEQ ID NO: 14.

The anti-CD47 monoclonal antibody provided by the present invention has a heavy chain type of IgG1, IgG3 or IgM; and its light chain type is κ.

The present invention also provides a nucleotide sequence encoding the anti-CD47 monoclonal antibody.

In some specific embodiments of the present invention, the nucleotide sequence comprises (I) a nucleotide sequence of the heavy chain variable region as represented by SEQ ID NOs: 15 to 21; a nucleotide sequence of the light chain variable region as represented by SEQ ID NOs: 22 to 28; or (II) a sequence complementary with the nucleotide sequence of the heavy chain variable region as represented by SEQ ID NOs: 15 to 21; a sequence complementary with the nucleotide sequence of the light chain variable region as represented by SEQ ID NOs: 22 to 28; or (III) a sequence which encodes the same protein as the nucleotide sequence of (I) or (II) but differs from the nucleotide sequence of (I) or (II) due to the degeneracy of the genetic code; or (IV) a sequence having at least 80% homology to the sequence of (I) or (II) or (III).

In some specific embodiments of the present invention, the nucleotide has a nucleotide sequence obtained by substituting or deleting one or more nucleotides of the nucleotide sequence represented by (I) or (II) or (Ill) or (IV) or adding one or more nucleotides to the nucleotide sequence represented by (I) or (II) or (III) or (IV), and having the same or similar function as the nucleotide sequence represented by (I) or (II) or (Ill) or (IV).

In some specific embodiments of the present invention, the nucleotide sequence has a nucleotide sequence obtained by substituting or deleting one or more nucleotides of the nucleotide sequence represented by (I) or (II) or (III) or (IV) or adding one or more nucleotides to the nucleotide sequence represented by (I) or (II) or (III) or (IV), and the more nucleotides are two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one or thirty-two nucleotides.

The present invention also provides an expression vector comprising a nucleotide sequence encoding an anti-CD47 monoclonal antibody provided by the present invention.

The present invention also provides a host cell transformed with the expression vector of the present invention.

The present invention also provides an antigen comprising the amino acid sequence represented by any one of SEQ ID NOs: 29 to 32.

The present invention also provides a hybridoma cell strain which produces the anti-CD47 monoclonal antibody of the present invention.

The preparation method of the anti-CD47 monoclonal antibody provided by the present invention comprises:

step 1: after immunizing a mouse with the antigen provided by the present invention, obtaining spleen cells of the mouse;

step 2: fusing the spleen cells with myeloma cells, screening for a hybridoma cell strain capable of binding to CD47, and culturing the obtained cell strain in vitro to obtain the anti-CD47 monoclonal antibody.

A combination made by marking the anti-CD47 monoclonal antibody of the present invention with a chemical marker or a biomarker.

The chemical marker is an isotope, an immunotoxin, and/or a chemical drug.

The biomarker is biotin, avidin or an enzyme label.

The present invention also provides a conjugate prepared by coupling the anti-CD47 monoclonal antibody or a combination thereof to a solid medium or a semi-solid medium.

Use of the anti-CD47 monoclonal antibody, the combination and/or the conjugate of the present invention in the preparation of a product for detecting the expression of CD47.

The present invention also provides a kit comprising the anti-CD47 monoclonal antibody, the combination and/or the conjugate.

A method for diagnosing disease comprises detecting the expression of CD47 using the kit provided by the present invention, and determining whether or not a disease is developed according to the expression level of CD47.

The disease is leukemia, lymphoma, breast cancer, lung cancer, gastric cancer, intestinal cancer, esophageal cancer, ovarian cancer, cervical cancer, kidney cancer, bladder cancer, pancreatic cancer, glioma and/or melanoma.

Use of the anti-CD47 monoclonal antibody, the combination and/or the conjugate of the present invention in the preparation of a formulation for blocking the binding of CD47 to SIRPα.

Use of the anti-CD47 monoclonal antibody, the combination and/or the conjugate of the present invention in the preparation of a formulation for increasing macrophage phagocytic index against tumor cells.

In an embodiment of the present invention, the tumor cells are human peripheral blood leukemia T cells.

Use of the anti-CD47 monoclonal antibody, the combination and/or the conjugate of the present invention in the preparation of a formulation for promoting apoptosis of tumor cells.

In an embodiment of the present invention, the tumor cells are human peripheral blood leukemia T cells.

Use of the anti-CD47 monoclonal antibody, the combination and/or the conjugate in the preparation of a medicament for preventing and treating disease.

The disease is leukemia, lymphoma, breast cancer, lung cancer, gastric cancer, intestinal cancer, esophageal cancer, ovarian cancer, cervical cancer, kidney cancer, bladder cancer, pancreatic cancer, glioma and/or melanoma.

The present invention also provides a medicament comprising the anti-CD47 monoclonal antibody of the present invention, a combination thereof and/or a conjugate thereof.

A method for preventing and treating disease, which comprises administering the medicament according to the present invention. The disease is leukemia, lymphoma, breast cancer, lung cancer, gastric cancer, intestinal cancer, esophageal cancer, ovarian cancer, cervical cancer, kidney cancer, bladder cancer, pancreatic cancer, glioma and/or melanoma.

The anti-CD47 monoclonal antibody provided by the present invention can effectively inhibit tumor growth. Blocking the signal between human SIRP and human CD47 may enhance macrophage phagocytosis of tumor cells, prevent the tumor cells from escaping a tumor immune defense system, and achieve an anti-tumor function. Blocking the binding of the CD47 on a tumor cell surface to SIRP on a macrophage surface may block a "do not eat me" signal from the tumor cell, promote the tumor cell recognition and uptake of macrophages, and thereby facilitating tumor cells to be phagocytosed. The binding of the CD47 on a tumor cell surface to SIRP on a macrophage surface is a common "do not eat me" signal. The anti-CD47 antibody can be used as a very promising target in the tumor immune system, and play a powerful and effective role in human cancer therapy.

BRIEF DESCRIPTION OF THE DRAWINGS

FIG. 1-A: lane 1: human CD47-linker peptide-hIgG1Fc; lane 2: human CD47-linker peptide-His; FIG. 1-B, lane 1: mouse CD47-linker peptide-hIgG1Fc; lane 2: mouse CD47-linker peptide-His.

SPECIFIC MODES FOR CARRYING OUT THE EMBODIMENTS

Figure 1:
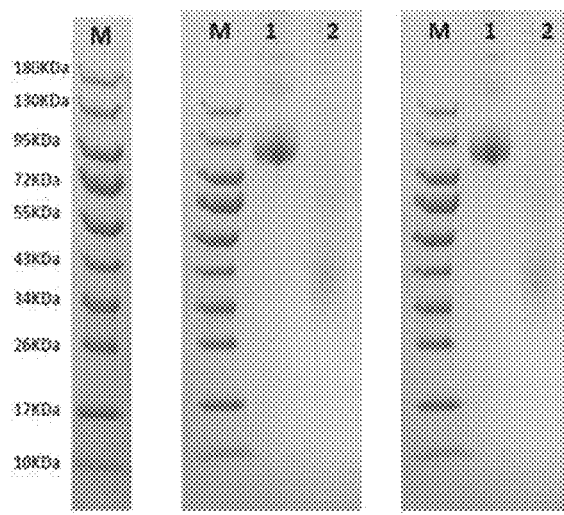
FIG. 1 shows SDS-PAGE electrophoresis detection of purified human and monkey CD47: lane M: protein molecular weight marker.

The present invention provides an anti-CD47 monoclonal antibody and use thereof, which can be achieved by a person skilled in the art by learning from the contents herein and appropriately improving the process parameters. It is to be understood that all such alternatives and modifications are obvious to a person skilled in the art and are considered to be included in the present invention. The method and the use according to the present invention have been described by the preferred embodiments, and it will be apparent to a person skilled in the art that the method and the use according to the present invention may be modified or appropriately altered and combined without departing from the scope, spirit and range of the present invention to achieve and apply the present invention.

"Antibody" refers to a protein composed of one or more polypeptides, which is capable of specifically binding an antigen. One form of antibody constitutes the basic structural unit of an antibody. This form is a tetramer consisting of two identical pairs of antibody chains, each pair having a light chain and a heavy chain. In each pair of antibody chains, the variable regions of the light chain and heavy chain are joined together to bind the antigen, while the constant region is responsible for the effector function of the antibody.

The "variable region" of an antibody heavy chain or light chain is the N-terminal mature region of the chain. Currently known types of antibodies include κ and λ light chains, as well as α, γ (IgG1, IgG2, IgG3, IgG4), δ, ε and μ heavy chains or equivalents thereof belonging to other types. The full length immunoglobulin "light chain" (approximately 25 kDa or approximately 214 amino acids) comprises a variable region formed by approximately 110 amino acids at the NH2-terminal, and a κ or λ constant region at the COOH-terminal. A full length immunoglobulin "heavy chain" (approximately 50 kDa or approximately 446 amino acids) also contains a variable region (approximately 116 amino acids) and one of the heavy chain constant regions, such as λ (approximately 330 amino acids).

"Antibody" includes any isotype of antibodies or immunoglobulins, or antibody fragments that retain the ability of specifically binding to an antigen, including but not limited to Fab, Fv, scFv and Fd fragments, chimeric antibodies, humanized antibodies, single chain antibodies, and a fusion protein comprising an antigen binding portion of an antibody and a non-antibody protein. The antibody can be labeled and detected, for example, by a radioisotope, an enzyme capable of producing a detectable substance, a fluorescent protein, biotin, or the like. Antibodies can also bind to a solid support, including but not limited to polystyrene plates or beads, and the like.

The present invention provides an anti-CD47 monoclonal antibody having a heavy chain variable region and a light chain variable region:

(I) the amino acid sequence of the heavy chain variable region is represented by SEQ ID NO: 1 or SEQ ID NO: 2 or SEQ ID NO: 3 or SEQ ID NO: 4 or SEQ ID NO: 5 or SEQ ID NO: 6 or SEQ ID NO: 7;

(II) the amino acid sequence of the light chain variable region is represented by SEQ ID NO: 8 or SEQ ID NO: 9 or SEQ ID NO: 10 or SEQ ID NO: 11 or SEQ ID NO: 12 or SEQ ID NO: 13 or SEQ ID NO: 14;

(III) an amino acid sequence obtained by substituting or deleting one or more amino acids of the amino acid sequence represented by (I) or (II) or by adding one or more amino acids to the amino acid sequence represented by (I) or (II), and having the same or similar function as the amino acid sequence represented by (I) or (II); or (IV) an amino acid sequence having at least 80% homology to the sequence represented by (I) or (II).

In some specific embodiments of the present invention, in said amino acid sequence obtained by substituting or deleting one or more amino acids of the amino acid sequence of the anti-CD47 monoclonal antibody or by adding one or more amino acids to the amino acid sequence of the anti-CD47 monoclonal antibody, the more amino acids are two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one or thirty-two amino acids.

The substitution occurs in a hypervariable region;

the hypervariable regions of the heavy chain variable region are HVR-H1, HVR-H2, and HVR-H3;

in SEQ ID NO: 2, the hypervariable region HVR-H1 sequence is represented by SEQ ID NO: 45; the HVR-H2 sequence is represented by SEQ ID NO: 46; and the HVR-H3 sequence is represented by SEQ ID NO: 47;

in SEQ ID NO: 5, the hypervariable region HVR-H1 sequence is represented by SEQ ID NO: 48; the HVR-H2 sequence is represented by SEQ ID NO: 49; and the HVR-H3 sequence is represented by SEQ ID NO: 50; and in SEQ ID NO: 6, the hypervariable region HVR-H1 sequence is represented by SEQ ID NO: 51; the HVR-H2 sequence is represented by SEQ ID NO: 52; and the HVR-H3 sequence is represented by SEQ ID NO: 53;

the hypervariable regions of the light chain variable region are HVR-L1, HVR-L2, and HVR-L3;

in SEQ ID NO: 9, the hypervariable region HVR-L1 sequence is represented by SEQ ID NO: 54; the HVR-L2 sequence is represented by SEQ ID NO: 55; and the HVR-L3 sequence is represented by SEQ ID NO: 56;

in SEQ ID NO: 12, the hypervariable region HVR-L1 sequence is represented by SEQ ID NO: 57; the HVR-L2 sequence is represented by SEQ ID NO: 58; and the HVR-L3 sequence is represented by SEQ ID NO: 59; and in SEQ ID NO: 13, the hypervariable region HVR-L1 sequence is represented by SEQ ID NO: 60; the HVR-L2 sequence is represented by SEQ ID NO: 61; and the HVR-L3 sequence is represented by SEQ ID NO: 62.

In some specific embodiments of the present invention, the anti-CD47 monoclonal antibody comprises:

(i) a heavy chain variable region with an amino acid sequence represented by SEQ ID NOs: 1, 2, 3, 4, 5, 6, or 7, and a light chain variable region with an amino acid sequence represented by SEQ ID NO: 8;

(ii) a heavy chain variable region with an amino acid sequence represented by SEQ ID NOs: 1, 2, 3, 4, 5, 6, or 7, and a light chain variable region with an amino acid sequence represented by SEQ ID NO: 9;

(iii) a heavy chain variable region with an amino acid sequence represented by SEQ ID NOs: 1, 2, 3, 4, 5, 6, or 7, and a light chain variable region with an amino acid sequence represented by SEQ ID NO: 10;

(iv) a heavy chain variable region with an amino acid sequence represented by SEQ ID NOs: 1, 2, 3, 4, 5, 6, or 7, and a light chain variable region with an amino acid sequence represented by SEQ ID NO: 11;

(V) a heavy chain variable region with an amino acid sequence represented by SEQ ID NOs: 1, 2, 3, 4, 5, 6, or 7, and a light chain variable region with an amino acid sequence represented by SEQ ID NO: 12;

(VI) a heavy chain variable region with an amino acid sequence represented by SEQ ID NOs: 1, 2, 3, 4, 5, 6, or 7, and a light chain variable region with an amino acid sequence represented by SEQ ID NO: 13;

(VII) a heavy chain variable region with an amino acid sequence represented by SEQ ID NOs: 1, 2, 3, 4, 5, 6, or 7, and a light chain variable region with an amino acid sequence represented by SEQ ID NO: 14.

The anti-CD47 monoclonal antibody provided by the present invention has a heavy chain type of IgG1, IgG3 or IgM; and its light chain type is κ.

Specifically, the amino acid sequence of the heavy chain variable region of the anti-CD47 monoclonal antibody is represented by SEQ ID NO: 1, and the amino acid sequence of the light chain variable region is represented by SEQ ID NO: 8.

Alternatively, the amino acid sequence of the heavy chain variable region of the anti-CD47 monoclonal antibody is represented by SEQ ID NO: 2, and the amino acid sequence of the light chain variable region is represented by SEQ ID NO: 8.

Alternatively, the amino acid sequence of the heavy chain variable region of the anti-CD47 monoclonal antibody is represented by SEQ ID NO: 3, and the amino acid sequence of the light chain variable region is represented by SEQ ID NO: 8.

Alternatively, the amino acid sequence of the heavy chain variable region of the anti-CD47 monoclonal antibody is represented by SEQ ID NO: 4, and the amino acid sequence of the light chain variable region is represented by SEQ ID NO: 8.

Alternatively, the amino acid sequence of the heavy chain variable region of the anti-CD47 monoclonal antibody is represented by SEQ ID NO: 5, and the amino acid sequence of the light chain variable region is represented by SEQ ID NO: 8.

Alternatively, the amino acid sequence of the heavy chain variable region of the anti-CD47 monoclonal antibody is represented by SEQ ID NO: 6, and the amino acid sequence of the light chain variable region is represented by SEQ ID NO: 8.

Alternatively, the amino acid sequence of the heavy chain variable region of the anti-CD47 monoclonal antibody is represented by SEQ ID NO: 7, and the amino acid sequence of the light chain variable region is represented by SEQ ID NO: 8.

Alternatively, the amino acid sequence of the heavy chain variable region of the anti-CD47 monoclonal antibody is represented by SEQ ID NO: 1, and the amino acid sequence of the light chain variable region is represented by SEQ ID NO: 9.

Alternatively, the amino acid sequence of the heavy chain variable region of the anti-CD47 monoclonal antibody is represented by SEQ ID NO: 2, and the amino acid sequence of the light chain variable region is represented by SEQ ID NO: 9.

Alternatively, the amino acid sequence of the heavy chain variable region of the anti-CD47 monoclonal antibody is represented by SEQ ID NO: 3, and the amino acid sequence of the light chain variable region is represented by SEQ ID NO: 9.

Alternatively, the amino acid sequence of the heavy chain variable region of the anti-CD47 monoclonal antibody is represented by SEQ ID NO: 4, and the amino acid sequence of the light chain variable region is represented by SEQ ID NO: 9.

Alternatively, the amino acid sequence of the heavy chain variable region of the anti-CD47 monoclonal antibody is represented by SEQ ID NO: 5, and the amino acid sequence of the light chain variable region is represented by SEQ ID NO: 9.

Alternatively, the amino acid sequence of the heavy chain variable region of the anti-CD47 monoclonal antibody is represented by SEQ ID NO: 6, and the amino acid sequence of the light chain variable region is represented by SEQ ID NO: 9.

Alternatively, the amino acid sequence of the heavy chain variable region of the anti-CD47 monoclonal antibody is represented by SEQ ID NO: 7, and the amino acid sequence of the light chain variable region is represented by SEQ ID NO: 9.

Alternatively, the amino acid sequence of the heavy chain variable region of the anti-CD47 monoclonal antibody is represented by SEQ ID NO: 1, and the amino acid sequence of the light chain variable region is represented by SEQ ID NO: 10.

Alternatively, the amino acid sequence of the heavy chain variable region of the anti-CD47 monoclonal antibody is represented by SEQ ID NO: 2, and the amino acid sequence of the light chain variable region is represented by SEQ ID NO: 10.

Alternatively, the amino acid sequence of the heavy chain variable region of the anti-CD47 monoclonal antibody is represented by SEQ ID NO: 3, and the amino acid sequence of the light chain variable region is represented by SEQ ID NO: 10.

Alternatively, the amino acid sequence of the heavy chain variable region of the anti-CD47 monoclonal antibody is represented by SEQ ID NO: 4, and the amino acid sequence of the light chain variable region is represented by SEQ ID NO: 10.

Alternatively, the amino acid sequence of the heavy chain variable region of the anti-CD47 monoclonal antibody is represented by SEQ ID NO: 5, and the amino acid sequence of the light chain variable region is represented by SEQ ID NO: 10.

Alternatively, the amino acid sequence of the heavy chain variable region of the anti-CD47 monoclonal antibody is represented by SEQ ID NO: 6, and the amino acid sequence of the light chain variable region is represented by SEQ ID NO: 10.

Alternatively, the amino acid sequence of the heavy chain variable region of the anti-CD47 monoclonal antibody is represented by SEQ ID NO: 7, and the amino acid sequence of the light chain variable region is represented by SEQ ID NO: 10.

Alternatively, the amino acid sequence of the heavy chain variable region of the anti-CD47 monoclonal antibody is represented by SEQ ID NO: 1, and the amino acid sequence of the light chain variable region is represented by SEQ ID NO: 11.

Alternatively, the amino acid sequence of the heavy chain variable region of the anti-CD47 monoclonal antibody is represented by SEQ ID NO: 2, and the amino acid sequence of the light chain variable region is represented by SEQ ID NO: 11.

Alternatively, the amino acid sequence of the heavy chain variable region of the anti-CD47 monoclonal antibody is represented by SEQ ID NO: 3, and the amino acid sequence of the light chain variable region is represented by SEQ ID NO: 11.

Alternatively, the amino acid sequence of the heavy chain variable region of the anti-CD47 monoclonal antibody is represented by SEQ ID NO: 4, and the amino acid sequence of the light chain variable region is represented by SEQ ID NO: 11.

Alternatively, the amino acid sequence of the heavy chain variable region of the anti-CD47 monoclonal antibody is represented by SEQ ID NO: 5, and the amino acid sequence of the light chain variable region is represented by SEQ ID NO: 11.

Alternatively, the amino acid sequence of the heavy chain variable region of the anti-CD47 monoclonal antibody is represented by SEQ ID NO: 6, and the amino acid sequence of the light chain variable region is represented by SEQ ID NO: 11.

Alternatively, the amino acid sequence of the heavy chain variable region of the anti-CD47 monoclonal antibody is represented by SEQ ID NO: 7, and the amino acid sequence of the light chain variable region is represented by SEQ ID NO: 11.

Alternatively, the amino acid sequence of the heavy chain variable region of the anti-CD47 monoclonal antibody is represented by SEQ ID NO: 1, and the amino acid sequence of the light chain variable region is represented by SEQ ID NO: 12.

Alternatively, the amino acid sequence of the heavy chain variable region of the anti-CD47 monoclonal antibody is represented by SEQ ID NO: 2, and the amino acid sequence of the light chain variable region is represented by SEQ ID NO: 12.

Alternatively, the amino acid sequence of the heavy chain variable region of the anti-CD47 monoclonal antibody is represented by SEQ ID NO: 3, and the amino acid sequence of the light chain variable region is represented by SEQ ID NO: 12.

Alternatively, the amino acid sequence of the heavy chain variable region of the anti-CD47 monoclonal antibody is represented by SEQ ID NO: 4, and the amino acid sequence of the light chain variable region is represented by SEQ ID NO: 12.

Alternatively, the amino acid sequence of the heavy chain variable region of the anti-CD47 monoclonal antibody is represented by SEQ ID NO: 5, and the amino acid sequence of the light chain variable region is represented by SEQ ID NO: 12.

Alternatively, the amino acid sequence of the heavy chain variable region of the anti-CD47 monoclonal antibody is represented by SEQ ID NO: 6, and the amino acid sequence of the light chain variable region is represented by SEQ ID NO: 12.

Alternatively, the amino acid sequence of the heavy chain variable region of the anti-CD47 monoclonal antibody is represented by SEQ ID NO: 7, and the amino acid sequence of the light chain variable region is represented by SEQ ID NO: 12.

Alternatively, the amino acid sequence of the heavy chain variable region of the anti-CD47 monoclonal antibody is represented by SEQ ID NO: 1, and the amino acid sequence of the light chain variable region is represented by SEQ ID NO: 13.

Alternatively, the amino acid sequence of the heavy chain variable region of the anti-CD47 monoclonal antibody is represented by SEQ ID NO: 2, and the amino acid sequence of the light chain variable region is represented by SEQ ID NO: 13.

Alternatively, the amino acid sequence of the heavy chain variable region of the anti-CD47 monoclonal antibody is represented by SEQ ID NO: 3, and the amino acid sequence of the light chain variable region is represented by SEQ ID NO: 13.

Alternatively, the amino acid sequence of the heavy chain variable region of the anti-CD47 monoclonal antibody is represented by SEQ ID NO: 4, and the amino acid sequence of the light chain variable region is represented by SEQ ID NO: 13.

Alternatively, the amino acid sequence of the heavy chain variable region of the anti-CD47 monoclonal antibody is represented by SEQ ID NO: 5, and the amino acid sequence of the light chain variable region is represented by SEQ ID NO: 13.

Alternatively, the amino acid sequence of the heavy chain variable region of the anti-CD47 monoclonal antibody is represented by SEQ ID NO: 6, and the amino acid sequence of the light chain variable region is represented by SEQ ID NO: 13.

Alternatively, the amino acid sequence of the heavy chain variable region of the anti-CD47 monoclonal antibody is represented by SEQ ID NO: 7, and the amino acid sequence of the light chain variable region is represented by SEQ ID NO: 13.

Alternatively, the amino acid sequence of the heavy chain variable region of the anti-CD47 monoclonal antibody is represented by SEQ ID NO: 1, and the amino acid sequence of the light chain variable region is represented by SEQ ID NO: 14.

Alternatively, the amino acid sequence of the heavy chain variable region of the anti-CD47 monoclonal antibody is represented by SEQ ID NO: 2, and the amino acid sequence of the light chain variable region is represented by SEQ ID NO: 14.

Alternatively, the amino acid sequence of the heavy chain variable region of the anti-CD47 monoclonal antibody is represented by SEQ ID NO: 3, and the amino acid sequence of the light chain variable region is represented by SEQ ID NO: 14.

Alternatively, the amino acid sequence of the heavy chain variable region of the anti-CD47 monoclonal antibody is represented by SEQ ID NO: 4, and the amino acid sequence of the light chain variable region is represented by SEQ ID NO: 14.

Alternatively, the amino acid sequence of the heavy chain variable region of the anti-CD47 monoclonal antibody is represented by SEQ ID NO: 5, and the amino acid sequence of the light chain variable region is represented by SEQ ID NO: 14.

Alternatively, the amino acid sequence of the heavy chain variable region of the anti-CD47 monoclonal antibody is represented by SEQ ID NO: 6, and the amino acid sequence of the light chain variable region is represented by SEQ ID NO: 14.

Alternatively, the amino acid sequence of the heavy chain variable region of the anti-CD47 monoclonal antibody is represented by SEQ ID NO: 7, and the amino acid sequence of the light chain variable region is represented by SEQ ID NO: 14.

In an embodiment of the present invention, the amino acid sequence of the heavy chain variable region of the anti-CD47 monoclonal antibody is represented by SEQ ID NO: 1, and the amino acid sequence of the light chain variable region is represented by SEQ ID NO: 8.

Alternatively, the amino acid sequence of the heavy chain variable region of the anti-CD47 monoclonal antibody is represented by SEQ ID NO: 2, and the amino acid sequence of the light chain variable region is represented by SEQ ID NO: 9.

Alternatively, the amino acid sequence of the heavy chain variable region of the anti-CD47 monoclonal antibody is represented by SEQ ID NO: 3, and the amino acid sequence of the light chain variable region is represented by SEQ ID NO: 10.

Alternatively, the amino acid sequence of the heavy chain variable region of the anti-CD47 monoclonal antibody is represented by SEQ ID NO: 4, and the amino acid sequence of the light chain variable region is represented by SEQ ID NO: 11.

Alternatively, the amino acid sequence of the heavy chain variable region of the anti-CD47 monoclonal antibody is represented by SEQ ID NO: 5, and the amino acid sequence of the light chain variable region is represented by SEQ ID NO: 12.

Alternatively, the amino acid sequence of the heavy chain variable region of the anti-CD47 monoclonal antibody is represented by SEQ ID NO: 6, and the amino acid sequence of the light chain variable region is represented by SEQ ID NO: 13.

Alternatively, the amino acid sequence of the heavy chain variable region of the anti-CD47 monoclonal antibody is represented by SEQ ID NO: 7, and the amino acid sequence of the light chain variable region is represented by SEQ ID NO: 14.

The heavy chain constant region of the antibody 059-1.82.1 of the present invention is mouse IgG3, the light chain constant region is the constant region of the mouse κ chain, and 059-1.30.1, 059-1.43.1, and 059-1.20.1 are all mouse IgG1, the light chain constant region is the constant region of the mouse κ chain; the heavy chain constant regions of 059-1.11.1, 059-1.51.2, and 059-1.100.5 are mouse IgM. The amino acid sequence of the heavy chain variable region is one of SEQ ID NOs: 1 to 7, and the amino acid sequence of the light chain variable region is one of SEQ ID NOs: 8 to 14.

The anti-CD47 monoclonal antibody provided by the present invention is capable of binding human CD47 and monkey CD47; in certain embodiments, the affinity between the antibody and its target is characterized by Ka, Kd (dissociation constant), and KD (equilibrium dissociation constant). The KD value of the antibody provided by the present invention is not higher than 30 nM.

The anti-CD47 monoclonal antibody provided by the present invention can block the binding between human SIRP and human CD47 in a dose-dependent manner; the blocking effect thereof is represented by an EC50 value, and the EC50 value of the antibody provided by the present invention is not less than 850 nM.

The anti-CD47 monoclonal antibody provided by the present invention is capable of binding to CD47 on cell surface; the detection of this effect is carried out by the FACS method, and the results of FACS are represented by MFI (fluorescence intensity), and the MFI value of the binding between the antibody provided by the present invention and the CD47 on cell surface is not less than 9547, and can be up to 18533.

The anti-CD47 monoclonal antibody provided by the present invention can promote macrophage phagocytosis of tumor cells, and the effect is measured by fluorescence imaging, and the result is expressed by the phagocytic index. The phagocytic index against jurkat cells of the antibody provided by the present invention can reach 79.

The anti-CD47 monoclonal antibody provided by the present invention can also induce apoptosis of tumor cells, and the effect is expressed by the cell apoptosis rate detected using a flow cytometry, and the results show that the antibody provided by the present invention can induce apoptosis of jurkat cells, and the apoptosis rate can reach 48%.

Jurkat cells belong to the acute T cell leukemia cell line and are one of a variety of malignant tumor cells. Like other malignant tumors, CD47 on the jurkat cell surface has a high expression level. In the present invention, it is proved by the experiment on jurkat cells that the CD47 monoclonal antibody provided by the present invention can prevent the tumor cells from escaping the tumor immune defense system by blocking the binding signal between SIRP and human CD47, and thereby achieving an anti-tumor effect.

In the monoclonal antibodies provided by the present invention, the monoclonal antibodies provided by the present invention with the amino acid sequence of the heavy chain variable region as represented by SEQ ID NO: 2 and the amino acid sequence of the light chain variable region as represented by SEQ ID NO: 9, the monoclonal antibodies with the amino acid sequence of the heavy chain variable region as represented by SEQ ID NO: 3 and the amino acid sequence of the light chain variable region as represented by SEQ ID NO: 10, the monoclonal antibodies with the amino acid sequence of the heavy chain variable region as represented by SEQ ID NO: 4 and the amino acid sequence of the light chain variable region as represented by SEQ ID NO: 11, and the monoclonal antibodies with the amino acid sequence of the heavy chain variable region as represented by SEQ ID NO: 6 and the amino acid sequence of the light chain variable region as represented by SEQ ID NO: 13, have a good affinity for both human CD47 and monkey CD47, can block the binding between CD47 and SIRPα, and can bind to CD47 on cell surface, promote macrophage phagocytosis of tumor cells, and induce apoptosis of tumor cells.

Wherein the monoclonal antibody with the amino acid sequence of the heavy chain variable region as represented by SEQ ID NO: 4 and the amino acid sequence of the light chain variable region as represented by SEQ ID NO: 11, has the best effect of blocking the binding between CD47 and SIRPα. This monoclonal antibody also has binding to CD47 on tumor cell surface, and the best effect of inducing macrophage phagocytosis of tumor cells. However, for inducing tumor cell apoptosis, the monoclonal antibody with the amino acid sequence of the heavy chain variable region as represented by SEQ ID NO: 3 and the amino acid sequence of the light chain variable region as represented by SEQ ID NO: 10 shows superior effect.

The present invention also provides a nucleotide sequence encoding the anti-CD47 monoclonal antibody.

In some embodiments of the present invention, the nucleotide sequence comprises:

(I) a nucleotide sequence of the heavy chain variable region as represented by SEQ ID NOs: 15 to 21; a nucleotide sequence of the light chain variable region as represented by SEQ ID NOs: 22 to 28; or (II) a sequence complementary with the nucleotide sequence of the heavy chain variable region as represented by SEQ ID NOs: 15 to 21; a sequence complementary with the nucleotide sequence of the light chain variable region as represented by SEQ ID NOs: 22 to 28; or (III) a sequence which encodes the same protein as the nucleotide sequence of (I) or (II) but differs from the nucleotide sequence of (I) or (II) due to the degeneracy of the genetic code; or (IV) a sequence having at least 80% homology to the sequence of (I) or (II) or (III).

In some specific embodiments of the present invention, the nucleotide sequence has a nucleotide sequence obtained by substituting or deleting one or more nucleotides of the nucleotide sequence represented by (I) or (II) or (III) or (IV) or by adding one or more nucleotides to the nucleotide sequence represented by (I) or (II) or (III) or (IV), and having the same or similar function as the nucleotide sequence represented by (I) or (II) or (Ill) or (IV).

In some specific embodiments of the present invention, the nucleotide sequence has a nucleotide sequence obtained by substituting or deleting one or more nucleotides of the nucleotide sequence represented by (I) or (II) or (III) or (IV) or by adding one or more nucleotides to the nucleotide sequence represented by (I) or (II) or (III) or (IV), and the more nucleotides are two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one or thirty-two nucleotides.

The present invention also provides an expression vector comprising a nucleotide sequence that provide a heavy chain variable region and/or a light chain variable region of the anti-CD47 monoclonal antibody provided by the present invention.

The present invention also provides a host cell transformed with the expression vector of the present invention.

The present invention also provides an antigen having the amino acid sequence represented by any one of SEQ ID NOs: 29 to 32.

The present invention also provides a hybridoma cell strain which produces the anti-CD47 monoclonal antibody of the present invention.

The preparation method of the anti-CD47 monoclonal antibody provided by the present invention comprises:

step 1: after immunizing a mouse with the antigen provided by the present invention, obtaining spleen cells of the mouse; and step 2: fusing the spleen cells with myeloma cells, screening for a hybridoma cell strain capable of binding to CD47, and culturing the cell strain in vitro to obtain an anti-CD47 monoclonal antibody.

In the present invention, the amino acid sequence of the antigen in step 1 is represented by SEQ ID NO: 29 or 31.

In the present invention, the antigen is mixed with an adjuvant to immunize mice.

The volume ratio of the antigen to the adjuvant is 1:1.

Specifically, the immunization is performed as follows: two weeks after a first immunization, a second immunization is performed, and 3 days later, a booster immunization is performed for the mice having a serum titer greater than 1:200,000.

The doses for the first immunization, the second immunization, and the booster immunization are all 10 μg in terms of antigen mass.

Immunization is performed by two-point injection.

The adjuvant for the first immunization is Freund's complete adjuvant, and the adjuvant for the second immunization and the booster immunization is Freund's incomplete adjuvant.

The mice used for immunization are BALB/C mice.

The myeloma cell is P3X63Ag8.653.

The fusion is performed at a ratio of spleen cells to myeloma cells of 5:1.

A HAT medium is used for screening.

Binding to CD47 specifically means the ability of binding to CD47 protein and the ability of binding to cells that express CD47 protein on the surface.

After identification, The CD47 monoclonal antibody prepared by the method of the present invention has a heavy chain type of IgG3, IgM or IgG, and a light chain type of K.

A combination made by marking the anti-CD47 monoclonal antibody of the present invention with a chemical marker or a biomarker.

The chemical marker is an isotope, an immunotoxin, and/or a chemical drug.

The biomarker is biotin, avidin or an enzyme label.

The enzyme label is preferably horseradish peroxidase or alkaline phosphatase.

The immunotoxin is preferably aflatoxin, diphtheria toxin, *Pseudomonas aeruginosa* exotoxin, ricin, abrin, mistletoe lectin, modeccin, PAP, saporin, gelonin or luffin.

The present invention also provides a conjugate prepared by coupling the anti-CD47 monoclonal antibody or a combination thereof to a solid medium or a semi-solid medium.

The solid medium or non-solid medium is selected from colloidal gold, polystyrene plates or beads.

Use of the anti-CD47 monoclonal antibody, the combination and/or the conjugate of the present invention in the preparation of a product for detecting the expression of CD47.

Experiments have shown that the CD47 monoclonal antibody provided by the present invention can bind to CD47 protein, and can also bind to cells expressing CD47 on the surface. Therefore, the CD47 monoclonal antibody provided by the present invention can be used for the detection of CD47 protein or cells expressing CD47 on the surface. Moreover, due to the high expression of the tumor cell surface marker CD47, the antibody provided by the present invention is capable of preparing a kit for the detection of the tumor surface marker CD47, wherein, the detection of the CD47 protein is carried out by a ELISA method, and the detection of cells expressing CD47 on the surface is carried out by a FACS method.

The present invention also provides a kit comprising the anti-CD47 monoclonal antibody, the combination and/or the conjugate.

The kit for detecting CD47 protein further includes a coating buffer, a washing solution, a blocking solution, and/or a color developing solution.

The coating buffer is a carbonate buffer.

The washing solution includes PBS, Tween, sodium chloride, potassium chloride, disodium hydrogen phosphate, and dipotassium hydrogen phosphate.

The blocking solution includes PBS and BSA.

The color developing solution includes a TMB solution, a substrate buffer, and a stop solution.

The substrate buffer includes citric acid and disodium hydrogen phosphate.

The stop solution is an aqueous hydrogen peroxide solution.

The kit for detecting cells expressing CD47 on the surface also include PBS, goat-anti-mouse IgG Fc and TITC secondary antibody.

Use of the anti-CD47 monoclonal antibody, the combination and/or the conjugate of the present invention in the preparation of a formulation for blocking the binding of CD47 to SIRPα.

The cells expressing CD47 on the surface are tumor cells.

The tumor cells are selected from leukemia cells, lymphoma cells, breast cancer cells, lung cancer cells, gastric cancer cells, intestinal cancer cells, esophageal cancer cells, ovarian cancer cells, cervical cancer cells, kidney cancer cells, bladder cancer cells, pancreatic cancer cells, glioma cells and/or melanoma cells.

A method for diagnosing disease comprises detecting CD47 expression using the kit provided by the present invention, and determining whether or not a disease is developed according to the expression level of CD47.

The disease is leukemia, lymphoma, breast cancer, lung cancer, gastric cancer, intestinal cancer, esophageal cancer, ovarian cancer, cervical cancer, kidney cancer, bladder cancer, pancreatic cancer, glioma and/or melanoma.

Use of the anti-CD47 monoclonal antibody, the combination and/or the conjugate of the present invention in the preparation of a formulation for blocking the binding of CD47 to SIRPα.

The anti-CD47 monoclonal antibody of the present invention blocks the binding of CD47 to SIRPα with an EC50 value of 850 nM to 2340 nM.

Use of the anti-CD47 monoclonal antibody, the combination and/or the conjugate of the present invention in the preparation of a formulation for increasing macrophage phagocytic index of tumor cells.

The dose of the anti-CD47 monoclonal antibody of the present invention for increasing macrophage phagocytic index of tumor cells is 10 g/mL in terms of antibody concentration.

In the embodiment of the present invention, the tumor cells are human peripheral blood leukemia T cells.

Use of the anti-CD47 monoclonal antibody, the combination and/or the conjugate of the present invention in the preparation of a formulation for promoting apoptosis of tumor cells.

In an embodiment of the present invention, the tumor cells are human peripheral blood leukemia T cells.

The dose of the anti-CD47 monoclonal antibody of the present invention for promoting apoptosis of tumor cells is 10 μg/mL.

Use of the anti-CD47 monoclonal antibody, combination and/or conjugate thereof in the preparation of a medicament for preventing and treating tumors.

The disease is leukemia, lymphoma, breast cancer, lung cancer, gastric cancer, intestinal cancer, esophageal cancer, ovarian cancer, cervical cancer, kidney cancer, bladder cancer, pancreatic cancer, glioma and/or melanoma.

The invention also provides a medicament comprising the anti-CD47 monoclonal antibody, the combination and/or conjugate of the present invention.

A method for preventing and treating disease comprises administering the medicament of the present invention. The disease is leukemia, lymphoma, breast cancer, lung cancer, gastric cancer, intestinal cancer, esophageal cancer, ovarian cancer, cervical cancer, kidney cancer, bladder cancer, pancreatic cancer, glioma and/or melanoma.

The medicament provided by the present invention can promote tumor cell recognition and uptake of macrophages by blocking a "do not eat me" signal from the tumor cells, thereby facilitating tumor cells to be phagocytosed.

The dosage form of the medicament provided by the present invention is an injection solution or a powder injection.

The concentration of the antibody in the injection solution is 10 μg/mL.

The anti-CD47 monoclonal antibody provided by the present invention can effectively inhibit tumor growth. Blocking the signal between human SIRP and human CD47 may enhance macrophage phagocytosis of tumor cells, prevent the tumor cells from escaping the tumor immune defense system, and have an anti-tumor function. Blocking the binding of the CD47 on a tumor cell surface to SIRP on a macrophage surface may block a "do not eat me" signal from the tumor cells, promote the tumor cell recognition and uptake of macrophages, and thereby facilitating tumor cells to be phagocytosed. The binding between the CD47 on tumor cell surface and SIRP on macrophage surface is a common "do not eat me" signal. The anti-CD47 antibody can be used as a very promising target in the tumor immune system, and play a powerful and effective role in human cancer therapy.

The instruments used in the present invention are all commercially available and can be purchased in the market.

The present invention is further illustrated below in combination with the Examples.

Example 1: Preparation of Antigenic Protein and Positive Control Antibody 1.1 Synthesis of Antigen Gene and Construction of Expression Vector:

The amino acid sequence of the extracellular region of the human-derived and monkey-derived CD47 protein was fused with the linker peptide-hIgG1Fc or the linker peptide-7his amino acid sequence, and the amino acid sequence was designed as represented by SEQ ID NOs: 29, 30, 31, and 32.

The amino acid sequences corresponding to the human and monkey CD47 protein extracellular region fusion protein (CD47ECD-linker peptide-hIgG1Fc or CD47ECD-linker peptide-7his) designed above were codon-optimized, for example, SEQ ID NOs: 33, 34, 35, and 36 were added with the Hind III restriction enzyme cutting site and the Kozak sequence GCCGCCACC at the 5' terminal, and were added with the stop codon TAG and EcoR I restriction enzyme cutting site at the 3' terminal, and the optimized DNA was synthesized by GenScript Biotech Corp. and cloned into a pUC57simple vector (provided by GenScript Biotech Corp.), to give pUC57simple-CD47-linker peptide-hIgG1Fc and/or CD47ECD-linker peptide-7his plasmids for human and monkey.

Followed by enzyme digestion (Hind III and EcoR I) of human and monkey plasmids pUC57simple-CD47-linker peptide-hIgG1Fc, pUC57simple-CD47ECD-linker peptide-7his and vector pcDNA3.1, the fusion gene fragments CD47-linker peptide-hIgG1Fc and CD47ECD-linker peptide-7his were recovered after electrophoresis and subjected to ligation with the pcDNA3.1 vector to construct the following expression plasmids:

pcDNA3.1-human CD47-linker peptide-hIgG1Fc;
pcDNA3.1-human CD47ECD-linker peptide-7his;
pcDNA3.1-monkey CD47-linker peptide-hIgG1Fc; and
pcDNA3.1-monkey CD47ECD-linker peptide-7his.

Gene synthesis of positive antibody (pAb) and construction of expression vector

The sequences of pAb antibodies were as follows:
PABH, as represented by SEQ ID NOs: 37 and 38; and
PABL, as represented by SEQ ID NOs: 39 and 40.

The amino acid sequences corresponding to the above antibody sequences was codon-optimized, and added with the Hind III restriction enzyme cutting site and the Kozak sequence GCCGCCACC at the 5' terminal, and added with the stop codon TAG and EcoR I restriction enzyme cutting site at the 3' terminal, and the optimized DNA was synthesized by GenScript Biotech Corp. and cloned into a pUC57simple vector (provided by GenScript Biotech Corp.), to give pUC57simple-PCABH and pUC57simple-PCABL plasmids.

Followed by enzyme digestion (Hind III and EcoR I) of plasmids pUC57simple-PCABH and pUC57simple-PCABL, the gene fragments PCABH and PCABL were recovered after electrophoresis, and then subjected to ligation with pcDNA3.1 vector to construct pcDNA3.1-PCABH and pcDNA3.1-PCABL.

1.2 Transient Transfetion and Expression

Transient transfetion and expression were performed for pcDNA3.1-PCABH,
pcDNA3.1-PCABL,
pcDNA3.1-human CD47-linker peptide-hIgG1Fc,
pcDNA3.1-human CD47ECD-linker peptide-7his,
pcDNA3.1-monkey CD47-linker peptide-hIgG1Fc, and
pcDNA3.1-monkey CD47ECD-linker peptide-7his.

Transient transfection and expression were performed in a Freestyle medium using FreeStyle™ 293F cells. Twenty-four hours prior to transfection, 293F cells with a concentration of $0.6 \times 10^6$ cells/ml were inoculated in a 125 ml beaker flask and subjected to shake cultivation at 37° C. and 130 rpm in a 5% $CO_2$ incubator. When the transfection was performed, 60 μL of 293fectin was added to 1 ml of OPtiMEM, mixed well, and incubated at room temperature for 5 minutes. At the same time, the light chains of the recombinant vectors, heavy chains of the recombinant vectors and transfection reagents were mixed at a ratio of 3:2:1 with a total DNA amount of 30 μg, and dissolved in 1 ml of OPtiMEM. Then, DNA and 293fectin were thoroughly mixed with a total volume of 2 ml, incubated at room temperature for 15 minutes, then all of the mixture was added to the cell culture wells, mixed well, and subjected to shake cultivation (at 130 rpm) at 37° C. in a 5% $CO_2$ incubator for 7 days. The culture solution was subjected to high-speed centrifugation and vacuum filtration through a microfiltration membrane.

1.3 Protein Purification

Purification was carried out using a Protein A column (protein purification liquid chromatography system/AKTA Purifier 10, GE) according to the method provided by the manufacturer to obtain a purified human PDL-1-mIgG2aFc fusion protein. An AKTA was washed with ultrapure water, and a 1 ml rProtianA Fast Flow prepacked column was connected to the AKTA. Washing: washing was performed with 5 column volumes of 1 M HAC. Equilibration: equilibration was performed with 5 column volumes of 20 mM PB 0.15 M NaCl (pH 7.0).

Loading: A cell expression supernatant sample was centrifuged at 1000 rpm for 5 min, the supernatant was taken and centrifuged at 8000 rpm for 30 min, after centrifugation, 20 ml of the supernatant was loaded, at a flow rate of 0.2 ml/min. Equilibration: equilibration was performed with 5 column volumes of 20 mM PB 0.15 M NaCl (pH 7.0) at 0.2 ml/min. Washing: washing was performed with 5 column volumes of 20 mM PB 1 M NaCl (pH 7.0). Equilibration: equilibration was performed with 5 column volumes of 20 mM PB 0.15 M NaCl (pH 7.0).

Figure 2:
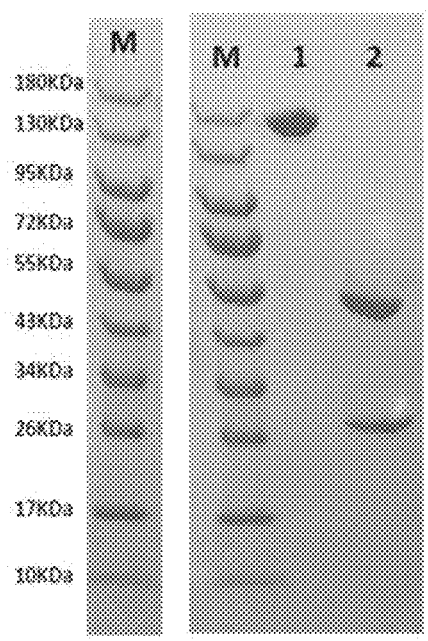
FIG. 2 shows SDS-PAGE electrophoresis detection of positive antibody (PAB): lane M: protein molecular weight marker; lane 1: non-reducing PAB; lane 2: reducing PAB.

Eluting: Eluting with 20 mM sodium citrate buffer (pH 3.0) at a flow rate of 0.2 ml/min. Collection was started when 100 mAu was reached under UV 280 and stopped when absorbance value decreased to 100 mAu. The pH of the sample was adjusted to pH 6 to 8 with 1 M Tris. The purified samples were shown in FIGS. 1 to 2.

Example 2: Preparation of Monoclonal Hybridoma

1. Immunization of Mice:

The immunogen human CD47-hFc (prepared in Example 1) was emulsified with adjuvant at a volume ratio of antigen to adjuvant of 1:1. A first immunization was performed by using Freund's complete adjuvant to emulsify the antigen, and after 2 weeks, a second immunization was started, the antigen was emulsified using Freund's incomplete adjuvant; immunization was performed by two-point injection, and the amount of antigen injected per mouse was 10 μg, and the volume of injection per injection point was 25 μL.

Three days after the second immunization, the mice were subjected to orbital blood collection, and a small amount of blood samples were taken for serum titer detection. After the serum titer detected by an indirect ELISA method reached 1:200,000 or above, a booster immunization is performed for the mice.

Immunizations were performed on a total of 3 groups, with 5 mice in each group.

2. Preparation of Feeder Cells and Myeloma Cells

Preparation of feeder cells: the abdominal skin of a normal BALB/C mouse (killed by cervical dislocation) was scissored to expose the peritoneum, a DMEM medium was sucked using a syringe, and injected into the peritoneal cavity of the mouse, peritoneal macrophages was washed and sucked out, and collected in a centrifuge tube for centrifugation at 1500 rmp/min for 3 min, and the lower brown precipitate was resuspended for subsequent use. The above procedures were repeated to obtain peritoneal macrophages from 3 normal mice.

Preparation of myeloma cells: P3X63Ag8.653 was thawed one week in advance, cultured in a complete medium containing 1× 8-azaguanine, and cultured with DMEM comprising 15% fetal bovine serum two days before fusion, and the confluence of P3X63Ag8.653 was maintained at 70%-80% till the day of fusion.

3. Cell Fusion and HAT Screening:

Acquisition and preparation of splenocytes: two mice (labeled as L1 and L2) after booster immunization was taken, after collecting the immune serums of L1 and L2, L1 and L2 were killed and immersed in 75% alcohol, the skin and peritoneum at the abdominal side of the immunized mice were scissored to expose the spleen, the surrounding tissues were removed with a scissor tip to obtain the spleen. After grinding with a grinding rod and filtering through a cell sieve, the spleen was prepared into a single cell suspension.

Pretreatment of cell fusion: P3X63Ag8.653 in a culture flask was collected, and centrifuged at 1000 rpm for 5 min, the supernatant was discarded; after resuspending, survival cells were counted, spleen cell suspension was centrifuged at 2000 rpm/5 min, the supernatant was discarded; after resuspending, survival cells was counted. The number of survival P3X63Ag8.653 cells and the number of survival spleen cells were recorded.

Cell fusion: the cells was mixed according to a ratio of spleen cells to P3X63Ag8.653 of 5:1, centrifuged at 2000 rpm for 5 min, the supernatant was discarded, the cell precipitate was shaken to disperse; 1 mL of preheated 50% PEG1500 solution was slowly dropwise added in a 37° C. water bath while swaying the bottom of the tube in the water at 37° C., with the above operation time being controlled at about 1 min; After standing for reacting for 30 s, a DMEM medium preheated at 37° C. was added into the tube in a manner from slow to fast addition, then the reaction was terminated. The cell suspension was centrifuged at 800 rpm for 3 min after the termination of the reaction, the supernatant was discarded, and the cell precipitate was gently shaken to disperse.

HAT medium screening: a HAT screening medium containing 1×HAT, 1×penicillin-streptomycin, 15% fetal bovine serum and 85% DMEM medium was prepared, mouse hybridoma cells and feeder cells were respectively resuspended in the above HAT screening medium, and then mixed. The obtained cell suspension was added into twenty 96-well cell culture plates at 300 μL/well, and cultured in a cell culture incubator at 37° C. After one week of culturing, the cell culture medium was replaced with HT medium for the first time, then cultured in a cell culture incubator at 37° C., and after three days of culturing, the culture medium was replaced HT medium for the second time.

4. Screening for Positive Cell Strains

Two weeks after the fusion, the cell supernatant was taken for a ELISA assay, and the binding status of the cell supernatant with the human CD47-his protein was detected. After the cells with positive ELISA results were selected, a second ELISA assay was performed. The cell supernatant with positive retest results was subjected to a FACS assay to detect the binding status of the cell supernatant to the CD47 protein on the surface of jurkat cells.

5. Amplification Culture

The cell strain detected as positive in both ELISA and FACS assays was transferred from a 96-well plate to a 24-well plate for culturing, and after confluence, transferred to a culture flask of 25 cm$^2$ for culturing.

6. Subcloning by Limited Dilution

The positive cell strains were mixed well by repeated pipetting, and a small amount was taken for survival cells count. About 100 cells were added into 40 mL of complete medium, mixed well, and sown in two plates. Additionally, about 100 cells were added into 20 mL of complete medium, mixed well and sown in one plate. About 1000 cells were added into 20 mL of complete medium, mixed well and sown in one plate. Samples were sown in totally four plates at three different cell densities: 0.5 cell/well, 1 cell/well, and 10 cells/well. The 96-well plates were placed in a 5% $CO_2$ incubator at 37° C. for culturing.

7. Clone Detection and Amplification Culture

The supernatant of the monoclonal cell well was taken for ELISA and FACS assay, and the binding status of the cell clonal antibody with the human and monkey CD47-his label and the binding status with the CD47 protein on the surface of jurkat cells were detected, respectively. The positive cell strains detected as positive in both ELISA and FACS (7 cell strains in total, respectively labeled as 059-1.11.1, 059-1.20.1, 059-1.30.1, 059-1.43.1, 059-1.51.2, 059-1.82.1, 059-1.100.5) were transferred from the 96-well plate to a 24-well plate for culturing, and after confluence, transferred to a 25 cm$^2$ culture flask for culturing.

8. Identification of Subclasses

A plate was coated with goat-anti-mouse IgG (Fc) at 2 μg/ml, 50 μL per well, stayed overnight at 4° C., and blocked with BSA; the supernatant of the cells to be detected was added at room temperature and incubated for 2 hours, enzyme-labeled subclass secondary antibodies IgG1, IgG2a, IgG2b, IgG2c, IgG3, κ, and λ (abcam) were added, color development was performed, and the absorbance was read at 450 nm, the subclass of the detected cell strains was determined as IgG3 or IgM or IgG1, and κ.

Wherein, the heavy chain constant region of the antibody 059-1.82.1 was mouse IgG3, the light chain constant region was the constant region of the mouse κ chain; the heavy chain constant regions of 059-1.30.1, 059-1.43.1 and 059-1.20.1 were mouse IgG1, the light chain constant regions were the constant region of the mouse κ chain; the heavy chain constant regions of 059-1.11.1, 059-1.51.2, and 059-1.100.5 were mouse IgM. The amino acid sequence of the heavy chain variable region was one of SEQ ID NOs: 1 to 7, and the amino acid sequence of the light chain variable region was one of SEQ ID NOs: 8 to 14.

Washing was performed with PBST for three times before each adding solution step.

9. Cell Cryopreservation

Preparation of cryopreservation solution: 90% fetal bovine serum, 10/o DMSO.

The cells in a culture flask were resuspended. After the cells were counted, centrifugation was performed at 1500 rpm/min for 3 min, and the supernatant was discarded; followed by suspending with fetal bovine serum containing 10% DMSO by repeated pipetting, the obtained suspension was cryopreserved in a cryopreservation box with 5×10$^6$ cells per tube, stayed overnight at −80° C., and transferred into liquid nitrogen on the next day.

10. Preservation of Genes of Monoclonal Hybridoma

RNA was extracted from a positive monoclonal cell strain RNA extraction solution, and was reverse transcribed into cDNA, which was permanently stored at −80° C.

Example 3 Preparation and Identification of Monoclonal Antibodies

1. Preparation of Antibodies by In Vitro Culture

The hybridoma cell strain prepared in Example 2 was thawed, and the method for thawing was as follows: the DMEM medium containing 10/o fetal bovine serum and 1% penicillin-streptomycin was thawed and cultured in a vial, after the cell confluence reaches about 90%, passage amplification culture was performed until a total of about 200 mL of the cell culture supernatant was reached.

2. Antibody Purification

Figure 3:
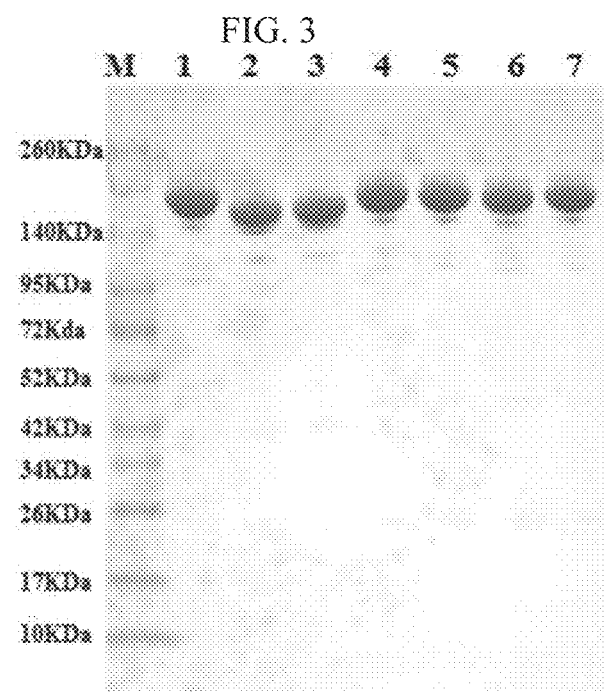
FIG. 3 shows non-reducing SDS-PAGE electrophoresis detection of a purified candidate antibody: lane M: protein molecular weight marker; lane 1: 059-1.11.1 purified antibody; lane 2: 059-1.20.1 purified antibody; lane 3: 059-1.30.1 purified antibody; lane 4: 059-1.43.1 purified antibody; lane 5: 059-1.51.2 purified antibody; lane 6: 059-1.82.1 purified antibody; lane 7: 059-1.100.5 purified antibody.

When cells were cultured for about 7 days, the cell supernatant was collected, the volume (about 200 mL) thereof was measured, NaCl was added to the supernatant to a concentration of 2.5 M; after vacuum filtering through a 0.22 μm mixed cellulose microfiltration membrane, the supernatant was stored at 4° C., and antibody purification was performed by Protein A affinity chromatography. Loading: the cell culture supernatant containing 2.5 M NaCl was filtered through a 0.22 μm filtration membrane, concentrated to 30 ml, and then directly loaded; washing: washing with 2.5 M PBS (pH 7.4) till UV280 baseline being 0; eluting: eluting with 0.1 M citric acid solution (pH 3.5). The eluent was collected in 2 ml for each fraction, 100 μL of 1 M Tris solution was added to each tube; and the collected solution was concentrated. Elution was performed with PBS until the ratio of the initial component was less than 0.1%. SDS-PAGE method was carried out to verify the purity of the purified antibody (FIG. 3).

Example 4 Gene Sequencing of Monoclonal Antibody and Preparation of Recombinant Antibody 1. Gene Sequencing of Monoclonal Antibody After immunization, fusion and monoclonalization, 059-1.11.1, 059-1.20.1, 059-1.30.1, 059-1.43.1, 059-1.51.2, 059-1.82.1, 059-1.100.5 were selected based on the results of affinity experiments, total RNA of monoclonal antibody cell strains was extracted, and reverse transcribed into cDNA, and then the heavy chain variable region and the light chain variable region of the antibody were amplified using PCR with the cDNA as a template.

Figure 4:
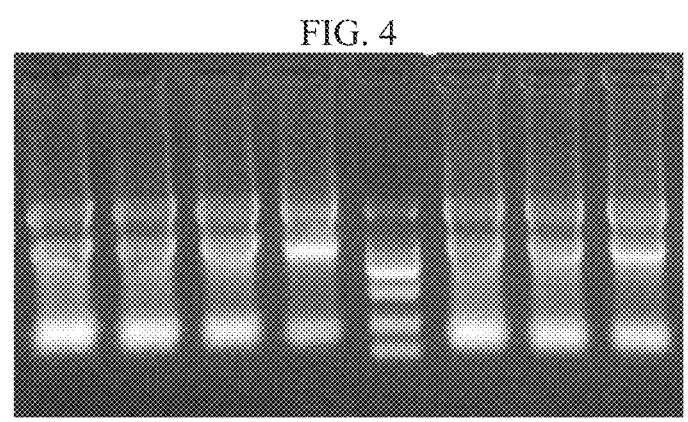
FIG. 4 shows electrophoresis of total RNA. Lane M: DL2000 molecular weight marker. Lanes 1-7 are total RNA electrophoresis bands of 059-1.11.1, 059-1.20.1, 059-1.30.1, 059-1.43.1, 059-1.51.2, 059-1.82.1, 059-1.100.5, respectively.

Sequence analysis of the heavy chain and the light chain of the antibody genes. The total RNA of 7 monoclonal antibody cell strain was extracted using Invitrogen's Trizol® reagent kit (15596-026) according to the instructions thereof. The extraction results were shown in FIG. 4.

Then, using Takara's 5'RACE FULL kit (D315), with the total RNA as a template, reverse transcription was performed to give a first chain cDNA using the random primers in the kit, then amplification of the heavy chain was performed using PCR with a primer designed for the constant region (mIgG R) and a linker primer in the kit, and the amplification of the light chain was performed using PCR with a primer designed for constant region (mIgK R) and a linker primer in the kit. The sequences of mIgG R and mIgK R were as follows:

```
mIgG R:
CTCAGgGAARTARCCYTTGAC;
(as represented by SEQ ID NO: 41)
and mIgk R:
TCACTGCCATCAATCTTCCAC.
(as represented by SEQ ID NO: 42)
```

Figure 5:
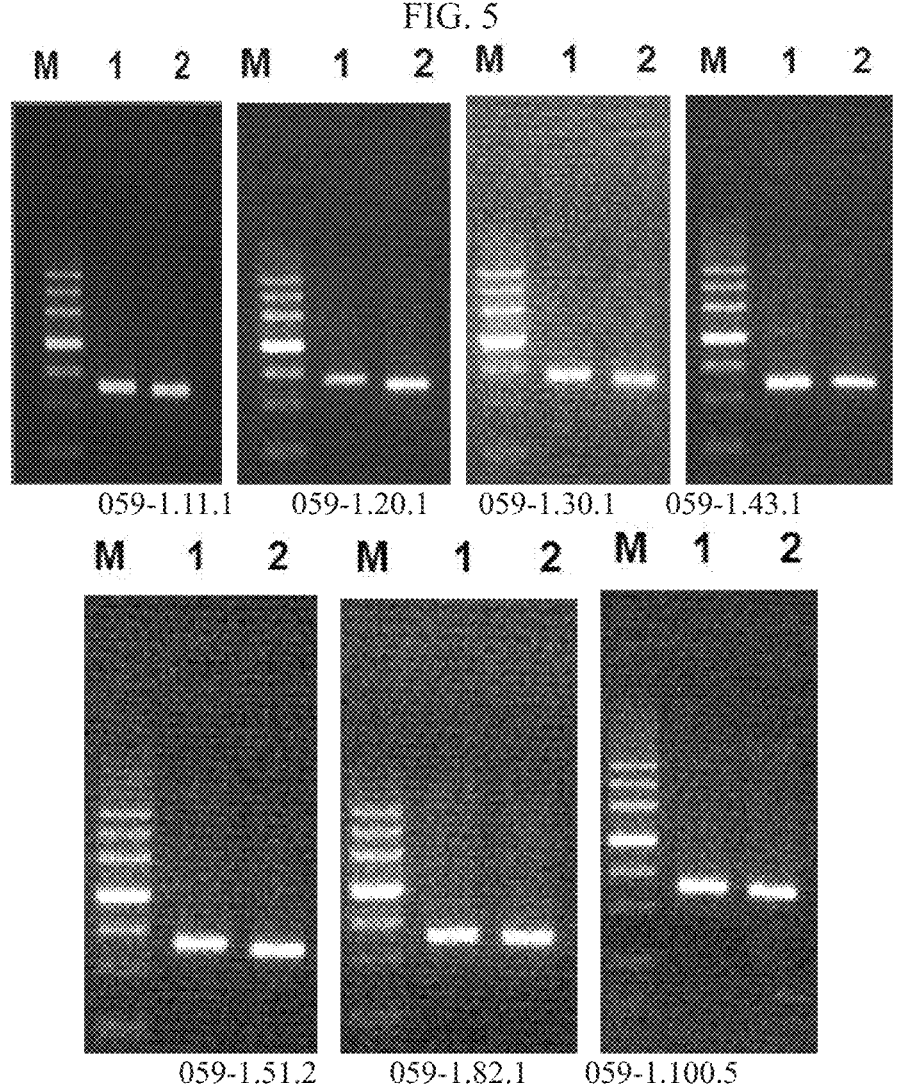
FIG. 5 shows agarose electrophoresis detection results of heavy chain variable region and light chain variable region of PCR amplified candidate antibodies.

The electrophoretic detection of the heavy chain variable region and the light chain variable region of the 7 monoclonal antibody cell strains after PCR amplification were shown in FIG. 5.

The PCR fragment was recovered using an agarose gel recovery kit, then TA cloning was performed, and a single clone was selected for PCR identification. The primers for identification were M13-F and M13-R, and some samples selected from the cell strains identified as correct were sent to Invitrogen for sequencing. The protein sequences of the heavy chain variable region were finally determined to be SEQ ID NOs: 1 to 7; the protein sequences of the light chain variable region were SEQ ID NOs: 8 to 14; the heavy chain nucleotide sequences were SEQ ID NOs: 15 to 21; and the light chain nucleotide sequences were SEQ ID NOs: 22 to 28.

```
Identification primer M13-F was as follows:
5'TGTAAAACGACGGCCAGT3'.
(as represented by SEQ ID NO: 43)

Identification primer m13-R was as follows:
5'CAGGAAACAGCTATGACC3',.
(as represented by SEQ ID NO: 44)
```

TABLE 1

| | Sequences | | | |
|---|---|---|---|---|
| | Amino acid sequences | | Nucleotide sequences | |
| | heavy chain variable region | light chain variable region | heavy chain variable region | light chain variable region |
| 059-1.100.5 | SEQ ID NO: 1 | SEQ ID NO: 8 | SEQ ID NO: 15 | SEQ ID NO: 22 |
| 059-1.82.1 | SEQ ID NO: 2 | SEQ ID NO: 9 | SEQ ID NO: 16 | SEQ ID NO:23 |
| 059-1.51.2 | SEQ ID NO: 3 | SEQ ID NO: 10 | SEQ ID NO: 17 | SEQ ID NO: 24 |
| 059-1.43.1 | SEQ ID NO: 4 | SEQ ID NO: 11 | SEQ ID NO: 18 | SEQ ID NO: 25 |
| 059-1.30.1 | SEQ ID NO: 5 | SEQ ID NO: 12 | SEQ ID NO: 19 | SEQ ID NO: 26 |
| 059-1.20.1 | SEQ ID NO: 6 | SEQ ID NO: 13 | SEQ ID NO: 20 | SEQ ID NO: 27 |
| 059-1.11.1 | SEQ ID NO: 7 | SEQ ID NO: 14 | SEQ ID NO: 21 | SEQ ID NO: 28 |

Example 5 Affinity Determination and Competitive ELISA Assay

1. Detection of Binding with Human CD47 (ELISA)

Coating: hCD47-his was diluted to 1 μg/ml with PBS, added to 96 wells of an ELISA plate with 100 μL per well, and incubated overnight at 4° C. Blocking: after the plate was washed for three times, it was blocked with 1% BSA+PBS at 300 μL per well, and incubated at room temperature for 2 hours. Addition of candidate antibody: after the plate was washed for three times, the cell culture supernatant of the candidate antibody or a positive control or a negative control was added at 100 μL per well, and incubated at room temperature for 2 hours. Addition of secondary antibody: after the plate was washed for three times, goat-anti-mouse IgG Fc and HRP (1:10000) were added at 100 μL per well, and reacted at room temperature for 1 hour. Color development: after the plate was washed for four times, a TMB color developing solution was added at 100 μL per well, followed by color development at room temperature in the dark for 10 minutes. Termination: the reaction was terminated by directly adding a stop solution with 100 μL per well.

Detection: immediately after termination of the reaction, the ELISA plate was placed in an ELISA reader, and the OD value was measured at 450 nm. The original data was saved as shown in Table 2 below:

TABLE 2

ELISA detected OD450 values of candidate clones and human CD47

| Antibody name | OD450 |
|---|---|
| 059-1.11.1 | 3.6718 |
| 059-1.20.1 | 4.0 |
| 059-1.30.1 | 4.0 |
| 059-1.43.1 | 4.0 |
| 059-1.51.2 | 0.7709 |
| 059-1.82.1 | 4.0 |
| 059-1.100.5 | 0.81 |
| Negative control | 0.086 |

2. Detection of Binding with Monkey CD47 (ELISA)

Coating: Monkey CD47-his was diluted to 1 μg/ml with PBS, added to 96 wells of an ELISA plate at 100 μL per well, and incubated overnight at 4° C. Blocking: after the plate was washed for three times, it was blocked with 1% BSA+PBS at 300 μL per well, and incubated at room temperature for 2 hours. Addition of candidate antibody: after the plate was washed for three times, the cell culture supernatant of the candidate antibody or a negative control was added at 100 μL per well, and incubated at room temperature for 2 hours. Addition of secondary antibody: after the plate was washed for three times, goat-anti-mouse IgG Fc and HRP (1:10000) were added at 100 μL per well, and reacted at room temperature for 1 hour. Color development: after the plate was washed for four times, a TMB color developing solution was added at 100 μL per well, followed by color development at room temperature in the dark for 10 minutes. Termination: the reaction was terminated by directly adding a stop solution at 100 μL per well. Detection: immediately after termination of the reaction, the ELISA plate was placed in an ELISA reader, and the OD value was measured at 450 nm. The original data was saved as shown in Table 3 below:

TABLE 3

ELISA detected OD values of candidate clones and monkey CD47

| Antibody name | OD450 |
|---|---|
| 059-1.11.1 | 4 |
| 059-1.20.1 | 4 |
| 059-1.30.1 | 4 |
| 059-1.43.1 | 4 |
| 059-1.51.2 | 0.6336 |
| 059-1.82.1 | 3.896 |
| 059-1.100.5 | 0.6166 |
| Negative control | 0.0883 |

3. Detection of Affinity with Human CD47 Protein

The affinity constant of the human CD47 antibody was detected using a Biacore T200 instrument; an anti-mouse Fc antibody (GE Healthcare Company, BR-1008-38) was coupled to a CM5 biosensor chip (GE Healthcare Company) via amino covalent binding, the anti-mouse Fc antibodies on the chip captured candidate monoclonal antibodies or positive control B6H12 (commercialized CD47 antibody, purchased from Abcam, catalog No. ab3283); human CD47 with different concentrations was flowed through the candidate antibody on the chip at a flow rate of 30 μL/min, and human CD47 bound with the candidate antibody with a binding time of 120 s and a dissociation time of 300 s. A dynamic fitting was performed using BIAevalution software (GE Healthcare Company), and 059-1.82.1 had the highest affinity. The obtained affinity constants were shown in Table 4 below.

TABLE 4

Determination results of affinity between candidate clones and human CD47

| Antibody name | Ka (1/Ms) | Kd(1/s) | KD(nM) |
|---|---|---|---|
| 059-1.11.1 | 2.60E5 | 0.004015 | 15.5 |
| 059-1.20.1 | 2.17E5 | 0.00548 | 25.3 |
| 059-1.30.1 | 4.24E5 | 0.01276 | 30.1 |
| 059-1.43.1 | 2.36E5 | 0.006657 | 28.3 |
| 059-1.51.2 | 3.70E5 | 0.01009 | 27.3 |
| 059-1.82.1 | 2.56E5 | 0.003643 | 14.2 |
| 059-1.100.5 | 1.57E5 | 0.0069 | 44.0 |
| Positive control | 1.32E5 | 0.003636 | 27.5 |

Example 6 Dose-Dependent Blocking of the Binding Between Human CD47 and Human SIRP (ELISA Method)

Figure 6:
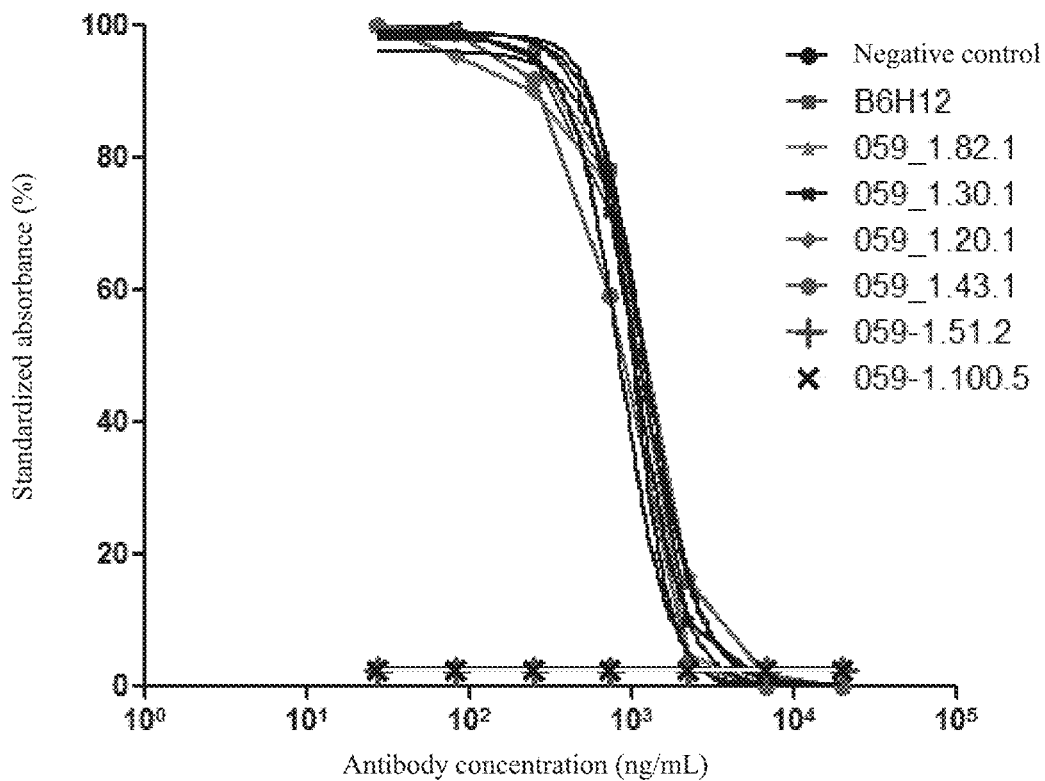
FIG. 6 is a graph showing the results of blocking human CD47 and SIRPα by antibodies 059-1.20.1, 059-1.30.1, 059-1.43.1, and 059-1.82.1.

Coating: Human CD47-hFc was diluted to 2 μg/ml with PBS, added to 96 wells of an ELISA plate at 100 μL per well, and incubated overnight at 4° C. Blocking: after the plate was washed for three times, it was blocked with 1% BSA+PBS at 300 μL per well, and incubated at room temperature for 1 hour. Mixing of candidate antibodies with SIRP-his: purified candidate antibodies were diluted to 20 μg/ml with PBST, and a 3-fold gradient dilution was performed with PBST solution, totally 7 gradients; human SIRP-his protein was diluted to 500 ng/mL with PBST, and the candidate antibodies with different dilution gradients were mixed with human SIRP-his protein at a ratio of 1:1, and incubated at room temperature for 30 min. Addition of a mixture of the candidate antibodies and human SIRP-his protein: 100 μL per well, reaction is performed at room temperature for 1 hour, and a mixture of a IgG isotype control and human SIRP-his protein was added to a control well. Addition of secondary antibody: after the plate was washed for three times, an anti-His tag antibody and HRP (1:3000) were added at 100 μL per well, and reacted at room temperature for 1 hour. Color development: after the plate was washed for four times, a TMB color developing solution was added at 100 μL per well, followed by color development at room temperature in the dark for 10 minutes. Termination: the reaction was terminated by directly adding a stop solution at 100 μL per well. Detection: immediately after termination of the reaction, the ELISA plate was placed in an ELISA reader, the OD value was measured at 450 nm, and the original data was saved. Data Processing: the original data was inputted into software SoftMax Pro 6.2.1 for data processing. The results were shown in Table 5 and FIG. 6 (the data in the figure was the final calculated data).

TABLE 5

Results about blocking the binding between CD47 and SIRP for candidate antibody

| Antibody name | EC50 (nM) |
|---|---|
| 059-1.11.1 | 2340 |
| 059-1.20.1 | 1190 |
| 059-1.30.1 | 1030 |

TABLE 5-continued

Results about blocking the binding between
CD47 and SIRP for candidate antibody

| Antibody name | EC50 (nM) |
| --- | --- |
| 059-1.43.1 | 850 |
| 059-1.51.2 | — |
| 059-1.82.1 | 1030 |
| 059-1.100.5 | — |
| Positive control | 1190 |
| Negative control | — |

The results showed that the candidate antibodies 059-1.11.1, 059-1.20.1, 059-1.30.1, 059-1.43.1 and 059-1.82.1 all had strong blocking effects, and 059-1.51.2 and 059-1.100.5 had no effects on blocking the binding of human CD47 to human SIRP.

Example 7 Determination of Binding to CD47 on Cell Surface (FACS Method)

Figure 7:
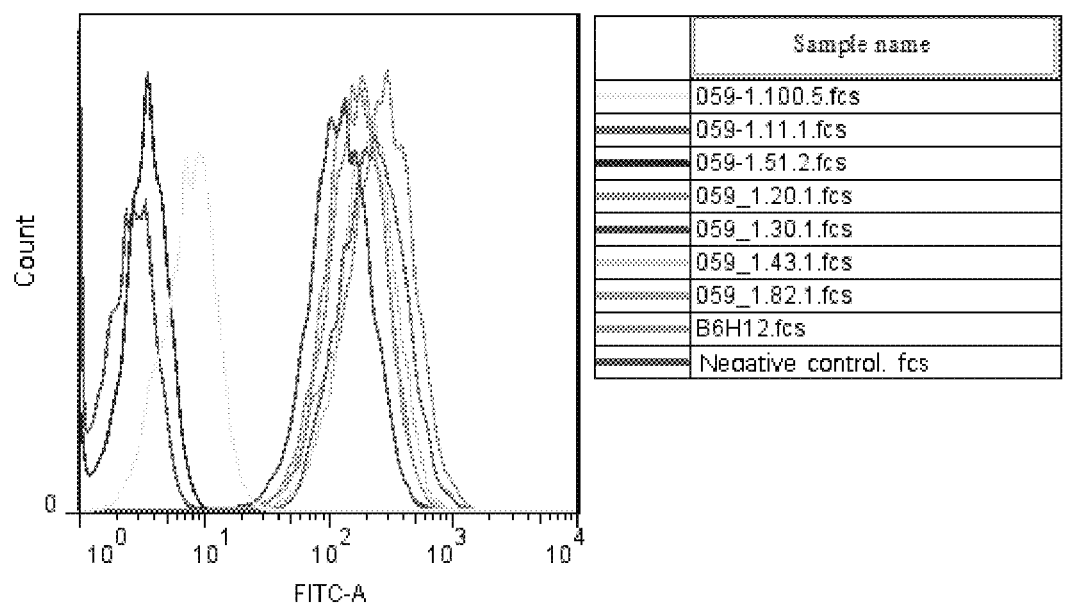
FIG. 7 shows FACS assays for binding of antibodies 059-1.20.1, 059-1.30.1, 059-1.43.1, 059-1.82.1 to CD47 on jurkat cell surface.

Jurkat cells were cultured and collected, subjected to centrifugation at 2000 rpm for 5 min, and washed once with PBS, and then survival cells was counted; $2.0 \times 10^5$ cells were added to each tube, and centrifuged at 2000 rpm for 5 min, the supernatant was discarded, 100 µL supernatant of candidate antibody cells was added to each tube, 100 µL of 1 ng/mL B6H12 antibody (commercialized CD47 antibody, purchased from Abcam, catalog No.: ab3283) was added to a positive control tube, 100 µL of DMEM medium was added to a negative control tube, and reacted at room temperature for 1 hour; centrifugation was carried out at 2000 rpm for 5 min, washing with PBS was performed for 3 times, 100 µL of 4 ng/mL goat-anti-mouse IgG Fc and FITC secondary antibody were added to each tube, and reacted at room temperature for 1 hour; centrifugation was carried out at 2000 rpm for 5 min, washing with PBS was performed for 3 times, 300 µL of PBS was added to each tube, and the obtained sample was transferred to a sample injection tube of a flow cytometer, and detection was performed on the flow cytometer. The results were shown in Table 6 and FIG. 7.

TABLE 6

Results about binding of candidate antibodies
with CD47 on the surface of Jurkat cells

| Antibody name | MFI |
| --- | --- |
| 059-1.11.1 | 6633 |
| 059-1.20.1 | 15315 |
| 059-1.30.1 | 9951 |
| 059-1.43.1 | 18533 |
| 059-1.51.2 | 144 |
| 059-1.82.1 | 9547 |
| 059-1.100.5 | 216 |
| Positive control (B6H12) | 13000 |
| Negative control | 57 |

The results showed that the candidate antibodies had significant binding activity to the CD47 on cell surface.

Example 8 Experiments about CD47 Antibody Mediated Phagocytosis of Jurkat Cells by Mouse Peritoneal Primary Macrophages 1. Preparation of C57 Mouse Peritoneal Primary Macrophages The animal was killed by cervical dislocation, with the mouse tail in hand, the whole mouse was immersed in 70% alcohol for 3 to 5 seconds. The animal was placed on a dissection table, the limbs were fixed with needles, with both hands holding forceps, the skin was torn apart and pulled to two sides to expose the peritoneum, the peritoneal wall was scrubbed with 70% alcohol, and then 10 ml of Eagle solution was injected into the abdominal cavity with a syringe, while the peritoneal wall was kneaded with fingers from both sides to allow the liquid to flow sufficiently in the abdominal cavity. The abdominal wall was gently picked up with a needle, so that the animal body slightly leaned to one side, and the liquid in the abdominal cavity was collected and sucked into the needle tube. The needle was carefully pulled out, and the liquid was injected into a centrifuge tube. Followed by centrifugation (250 g) at 4° C. for 4 minutes, the supernatant was discarded, and 10 ml of Eagle medium was added, and survival cells were counted. In order to obtain $3 \times 10^5$ attached cells per square centimeter, cells were inoculated at a final concentration of $2.5 \times 10^6$/ml. In order to purify the cultured cells and remove other leukocyte, several hours after inoculation, the culture solution was removed, the rest was washed with Eagle solution for 1 to 2 times, then a fresh Eagle culture solution was added, and cultivation was performed at 37° C. in a 5% $CO_2$ incubator.

2. Macrophage Phagocytosis Experiment

Figure 8:
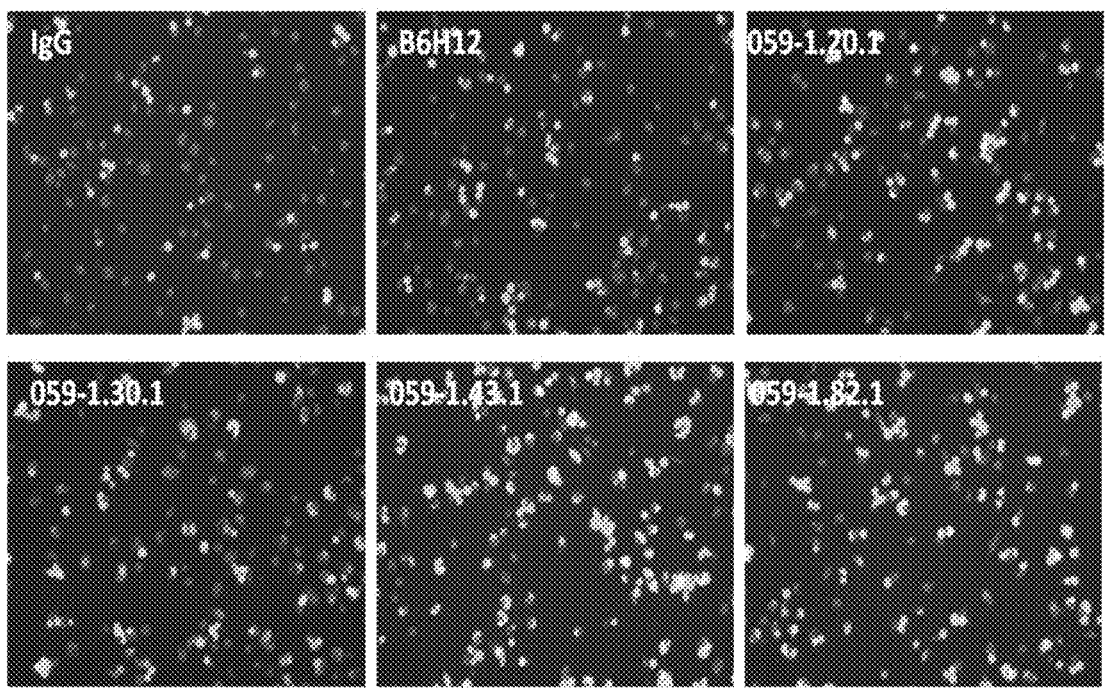
FIG. 8 shows that antibodies 059-1.20.1, 059-1.30.1, 059-1.43.1, 059-1.82.1 promote mouse peritoneal primary macrophages's phagocytosis of Jurkat cells.

The effect of CD47 antibody prepared in Example 5 on the phagocytosis of Jurkat cells by C57BL mouse peritoneal primary macrophages was examined by fluorescence imaging. Mouse macrophages were stained with PKH26 dye one day in advance (4 micromoles, 5 min), and inoculated in a 96-well plate at 20,000 cells/well; the next day, Jurkat cells (2 micromoles, 10 min) were stained with CFSE dye, after washing, the Jurkat cells were resuspended in a serum-free medium and added to macrophages at 80,000 cells/well. 2 hours before the Jurkat cells were inoculated, the serum-containing medium for macrophages was replaced with a serum-free medium and various antibodies were added to the suspension of two cells at a concentration of 10 µg/ml. After 2 hours of culturing, Jurkat cells that were not phagocytized were washed away, and after cell imaging by fluorescence microscopy, the level of the effect of CD47 antibody on promoting phagocytosis were quantified by counting how many Jurkat cells were phagocytized per 100 macrophages, i.e., phagocytic index. The results were shown in FIG. 8 (a graph showing phagocytic effect) and Table 7 (phagocytic index). As reported by literatures, B6H12 (commercialized CD47 antibody, purchased from Abcam, catalog No.: ab3283) has a weaker effect on promoting phagocytosis. Four selected antibody molecules in Example 5 have a good effect on promoting phagocytosis, especially 059-1.30.1, 059-1.43.1, and 059-1.82.1.

TABLE 7

CD47 antibodies promote macrophage phagocytosis of Jurkat cells

| Antibody name | phagocytic index |
| --- | --- |
| 059-1.20.1 | 43 |
| 059-1.30.1 | 70 |

TABLE 7-continued

CD47 antibodies promote macrophage phagocytosis of Jurkat cells

| Antibody name | phagocytic index |
|---|---|
| 059-1.43.1 | 79 |
| 059-1.82.1 | 74 |
| Positive control (B6H12) | 20 |
| Negative control | 0 |

Example 9 In Vitro Induction of Apoptosis of Jurkat Cells by CD47 Antibody

Jurkat cells at logarithmic growth phase were collected, and washed with a serum-free medium, a single cell suspension was prepared with 5% FBS-1640, and the cells were resuspended to $10 \times 10^5$/ml, and added to a 24-well plate for culturing at $5 \times 10^5$/well, i.e., 500 µL/well. The experiment was designed as follows: CD47 antibody (final concentration: 10 µg/ml) was added at 50 µL/well, an anti-Fas positive control well was set, and the same volume of medium was added to the wells without the addition of antibodies. After 5 h, the cell suspension was collected into a 1.5 ml EP tube and centrifuged (500 g×5 min). The supernatant was discarded, cells were resuspended with 100 µL of PBS and mixed well in each tube, and the cells were stained with annexin-V (Roche Diagnostics) at 4° C. in the dark for 30 minutes. Washing with PBS was performed for three times, 500 µL of PBS was added to each tube to resuspend and mix cells, and PI (final concentration of 1 µg/ml) was added 10 to 15 min before loading on a flow cytometer. Measuring the ratio of annexin-V positive cells and annexin-V and PI double positive cells to the total cells (i.e., the apoptotic rate of Jurkat cells) was performed on the flow cytometer.

TABLE 8

CD47 antibody induced apoptosis of Jurkat cells

| Antibody name | Apoptotic rate (%) |
|---|---|
| 059-1.20.1 | 33 |
| 059-1.30.1 | 48 |
| 059-1.43.1 | 37 |
| 059-1.82.1 | 24 |
| Control antibody (B6H12) | 8 |
| Negative control | 5 |

B6H12 did not induce apoptosis of Jurkat cells, while four tested 059 antibodies showed induction of apoptosis of Jurkat cells in different degrees, and 059-1.30.1 had the strongest effect. 059-1.30.1 showed the best effect on promoting macrophage phagocytosis and inducing apoptosis of Jurkat cells.

The above are only preferred embodiments of the present invention, and it should be noted that a person skilled in the art can also make various improvements and modifications without departing from the principles of the present invention. These improvements and modifications should also be considered to be within the scope of protection of the present invention.

What is claimed is:

1. An anti-CD47 monoclonal antibody, characterized in that, the antibody comprises a heavy chain variable region and a light chain variable region, wherein:
   (I) the amino acid sequence of the heavy chain variable region is represented by SEQ ID NO: 1 or SEQ ID NO: 2 or SEQ ID NO: 3 or SEQ ID NO: 4 or SEQ ID NO: 5 or SEQ ID NO: 6 or SEQ ID NO: 7; and
   (II) the amino acid sequence of the light chain variable region is represented by SEQ ID NO: 8 or SEQ ID NO: 9 or SEQ ID NO: 10 or SEQ ID NO: 11 or SEQ ID NO: 12 or SEQ ID NO: 13 or SEQ ID NO: 14.

2. The anti-CD47 monoclonal antibody according to claim 1, wherein:
   (i) the heavy chain variable region with the amino acid sequence is represented by SEQ ID NO: 4, and
   (ii) the light chain variable region with the amino acid sequence is represented by SEQ ID NO: 11.

3. The anti-CD47 monoclonal antibody according to claim 1, characterized in that,
   the hypervariable regions of the heavy chain variable region are HVR-H1 HVR-H2, and HVR-H3;
   in SEQ ID NO: 2, the hypervariable region HVR-H1 sequence is represented by SEQ ID NO: 45; the HVR-H2 sequence is represented by SEQ ID NO: 46; and the HVR-H3 sequence is represented by SEQ ID NO: 47;
   in SEQ ID NO: 5, the hypervariable region HVR-H1 sequence is represented by SEQ ID NO: 48; the HVR-H2 sequence is represented by SEQ ID NO: 49; and the HVR-H3 sequence is represented by SEQ ID NO: 50; and
   in SEQ ID NO: 6, the hypervariable region HVR-H1 sequence is represented by SEQ ID NO: 51; the HVR-H2 sequence is represented by SEQ ID NO: 52; and the HVR-H3 sequence is represented by SEQ ID NO: 53;
   the hypervariable regions of the light chain variable region are HVR-L1, HVR-L2, and HVR-L3;
   SEQ ID NO: 9, the hypervariable region HVR-L1 sequence is represented by SEQ ID NO: 54; the HVR-L2 sequence is represented by SEQ ID NO: 55; and the HVR-L3 sequence is represented by SEQ ID NO: 56;
   in SEQ ID NO: 12, the hypervariable region HVR-L1 sequence is represented by SEQ ID NO: 57; the HVR-L2 sequence is represented by SEQ ID NO: 58; and the HVR-L3 sequence is represented by SEQ ID NO: 59; and
   in SEQ ID NO: 13, the hypervariable region HVR-L1 sequence is represented by SEQ ID NO: 60; the HVR-L2 sequence is represented by SEQ ID NO: 61; and the HVR-L3 sequence is represented by SEQ ID NO: 62.

4. The anti-CD47 monoclonal antibody according to claim 1,
   wherein:
   (i) the heavy chain variable region is represented by SEQ ID NO: 5, and
   (ii) the light chain variable region is represented by SEQ ID NO: 12.

5. A medicament, characterized in that, it comprises the anti-CD47 monoclonal antibody according to claim 1.

6. The anti-CD47 monoclonal antibody according to claim 1, wherein:
   (i) the heavy chain variable region is represented by SEQ ID NO: 2, and
   (ii) the light chain variable region is represented by SEQ ID NO: 9.

7. The anti-CD47 monoclonal antibody according to claim 6, characterized in that, the heavy chain type is IgG1, IgG3 or IgM; and the light chain type is κ.

8. A hybridoma cell strain, which produces the anti-CD47 monoclonal antibody according to claim 6.

9. The anti-CD47 monoclonal antibody according to claim 1, wherein:
   (i) the amino acid sequence of the heavy chain variable region is represented by SEQ ID NO: 6, and
   (ii) the amino acid sequence of the light chain variable region is represented by SEQ ID NO: 13.

10. The anti-CD47 monoclonal antibody according to claim 9, characterized in that, the heavy chain type is IgG1, IgG3 or IgM; and the light chain type is κ.

11. A hybridoma cell strain, which produces the anti-CD47 monoclonal antibody according to claim 9.

* * * * *

SEQUENCE LISTING

<160> NUMBER OF SEQ ID NOS: 62

<210> SEQ ID NO 1
<211> LENGTH: 136
<212> TYPE: PRT
<213> ORGANISM: Artificial sequence
<220> FEATURE:
<223> OTHER INFORMATION: Laboratory synthesis

<400> SEQUENCE: 1

```
Met Glu Trp Ser Trp Val Phe Leu Phe Leu Leu Ser Val Ile Ala Gly
1               5                   10                  15

Val Gln Ser Gln Val Gln Leu Gln Gln Ser Gly Ala Glu Leu Val Arg
            20                  25                  30

Pro Gly Ala Ser Val Thr Leu Ser Cys Lys Ala Ser Gly Tyr Thr Phe
        35                  40                  45

Thr Asp Tyr Glu Met His Trp Val Lys Gln Thr Pro Val His Gly Leu
    50                  55                  60

Glu Trp Ile Gly Ala Ile Asp Pro Glu Thr Gly Gly Thr Ala Tyr Asn
65                  70                  75                  80

Gln Asn Phe Lys Gly Lys Ala Thr Leu Thr Ala Asp Lys Ser Ser Ser
                85                  90                  95

Thr Ala Tyr Met Glu Leu Arg Ser Leu Thr Ser Glu Asp Ser Ala Val
            100                 105                 110

Tyr Tyr Cys Thr Arg Gly Thr Pro Tyr Ala Met Asp Tyr Trp Gly Gln
        115                 120                 125

Gly Thr Ser Val Thr Val Ser Ser
    130                 135
```

<210> SEQ ID NO 2
<211> LENGTH: 136
<212> TYPE: PRT
<213> ORGANISM: Artificial sequence
<220> FEATURE:
<223> OTHER INFORMATION: Laboratory synthesis

<400> SEQUENCE: 2

Met Glu Trp Ser Trp Ile Phe Leu Phe Leu Leu Ser Gly Thr Ala Gly
1               5                   10                  15

Val His Ser Glu Val Gln Leu Gln Gln Ser Gly Pro Glu Leu Val Lys
            20                  25                  30

Pro Gly Ala Ser Val Lys Met Ser Cys Lys Ala Ser Gly Tyr Thr Phe
        35                  40                  45

Thr Asn Tyr Val Met His Trp Val Lys Gln Lys Pro Gly Gln Gly Leu
    50                  55                  60

Glu Trp Ile Gly Tyr Ile Asn Pro Tyr Asn Asp Gly Thr Asn Tyr Asn
65                  70                  75                  80

Glu Lys Phe Lys Gly Lys Ala Thr Leu Thr Ser Asp Lys Ser Ser Ser
                85                  90                  95

Thr Ala Tyr Met Glu Leu Ser Ser Leu Thr Ser Glu Asp Ser Ala Val
            100                 105                 110

Tyr Tyr Cys Ala Lys Gly Gly Trp Phe Ser Met Asp Tyr Trp Gly Gln
        115                 120                 125

Gly Thr Ser Val Thr Val Ser Ser
    130                 135

<210> SEQ ID NO 3
<211> LENGTH: 136
<212> TYPE: PRT
<213> ORGANISM: Artificial sequence
<220> FEATURE:
<223> OTHER INFORMATION: Laboratory synthesis

<400> SEQUENCE: 3

Met Glu Trp Ser Trp Ile Phe Leu Phe Leu Leu Ser Gly Thr Ala Gly
1               5                   10                  15

Val His Ser Glu Val Gln Leu Gln Gln Ser Gly Pro Glu Leu Val Lys
            20                  25                  30

Pro Gly Ala Ser Val Lys Met Ser Cys Lys Ala Ser Gly Tyr Thr Phe
        35                  40                  45

Thr Asn Tyr Val Met His Trp Met Lys Gln Lys Pro Gly Gln Gly Leu
    50                  55                  60

Glu Trp Ile Gly Tyr Ile Asn Pro Tyr Asn Asp Asp Thr Lys Tyr Asn
65                  70                  75                  80

Glu Lys Phe Lys Asp Arg Ala Thr Leu Thr Ser Asp Lys Ser Ser Ser
                85                  90                  95

Thr Ala Tyr Met Glu Leu Ser Ser Leu Thr Ser Glu Asp Ser Ala Val
            100                 105                 110

Tyr Tyr Cys Ala Lys Gly Gly Tyr Tyr Ser Met Asp Tyr Trp Gly Gln
        115                 120                 125

Gly Thr Ser Val Thr Val Ser Ser
    130                 135

<210> SEQ ID NO 4
<211> LENGTH: 136
<212> TYPE: PRT
<213> ORGANISM: Artificial sequence
<220> FEATURE:

-continued

<223> OTHER INFORMATION: Laboratory synthesis

<400> SEQUENCE: 4

Met Glu Trp Ser Trp Val Phe Leu Phe Leu Ser Val Ile Ala Gly
1               5                   10                  15

Val Gln Ser Gln Val Gln Leu Gln Gln Ser Gly Ala Glu Leu Val Arg
            20                  25                  30

Pro Gly Ala Ser Val Thr Leu Ser Cys Lys Ala Ser Gly Tyr Thr Phe
        35                  40                  45

Thr Asp Tyr Glu Met His Trp Val Lys Gln Thr Pro Val His Gly Leu
    50                  55                  60

Glu Trp Ile Gly Ala Ile Asp Pro Glu Thr Gly Gly Thr Ala Tyr Asn
65                  70                  75                  80

Gln Lys Phe Lys Gly Lys Ala Thr Leu Thr Ala Asp Lys Ser Ser Ser
                85                  90                  95

Thr Ala Tyr Met Glu Leu Arg Ser Leu Thr Ser Glu Asp Ser Ala Val
            100                 105                 110

Tyr Tyr Cys Thr Arg Gly Thr Pro Tyr Ala Met Asp Tyr Trp Gly Gln
        115                 120                 125

Gly Thr Ser Val Thr Val Ser Ser
    130                 135

<210> SEQ ID NO 5
<211> LENGTH: 136
<212> TYPE: PRT
<213> ORGANISM: Artificial sequence
<220> FEATURE:
<223> OTHER INFORMATION: Laboratory synthesis

<400> SEQUENCE: 5

Met Glu Trp Ser Trp Ile Phe Leu Phe Leu Leu Ser Gly Thr Ala Gly
1               5                   10                  15

Val His Ser Glu Val Gln Leu Gln Gln Ser Gly Pro Glu Leu Val Lys
            20                  25                  30

Pro Gly Ala Ser Val Arg Met Ser Cys Lys Ala Ser Gly Tyr Thr Phe
        35                  40                  45

Thr Asn Tyr Val Met His Trp Val Lys Gln Lys Pro Gly Gln Gly Leu
    50                  55                  60

Glu Trp Ile Gly Tyr Ile Asn Pro Tyr Asn Asp Gly Thr Lys Tyr Ser
65                  70                  75                  80

Glu Lys Phe Lys Gly Lys Ala Thr Leu Thr Ser Asp Lys Ser Ser Ile
                85                  90                  95

Thr Ala Tyr Met Glu Leu Ser Ser Leu Thr Ser Glu Asp Ser Ala Val
            100                 105                 110

Tyr Tyr Cys Ala Lys Gly Gly Leu Phe Thr Phe Asp Tyr Trp Gly Gln
        115                 120                 125

Gly Thr Thr Leu Thr Val Ser Ser
    130                 135

<210> SEQ ID NO 6
<211> LENGTH: 136
<212> TYPE: PRT
<213> ORGANISM: Artificial sequence
<220> FEATURE:
<223> OTHER INFORMATION: Laboratory synthesis

<400> SEQUENCE: 6

Met Glu Trp Ser Trp Ile Phe Leu Phe Leu Leu Ser Gly Thr Ala Gly

```
                1               5                  10                  15
Val His Ser Glu Val Gln Leu Gln Gln Ser Gly Pro Glu Leu Val Lys
                        20                  25                  30

Pro Gly Ala Ser Val Asn Met Ser Cys Lys Ala Ser Gly Tyr Thr Phe
                35                  40                  45

Thr Asn Tyr Phe Leu His Trp Val Lys Gln Lys Pro Gly Gln Gly Leu
         50                  55                  60

Glu Trp Ile Gly Tyr Ile Asn Pro Tyr Asn Asp Gly Thr Asn Tyr Asn
 65                  70                  75                  80

Glu Asn Phe Lys Gly Lys Ala Thr Leu Thr Ser Asp Lys Ser Ser Ser
                 85                  90                  95

Thr Ala Tyr Met Glu Leu Ser Ser Leu Thr Ser Glu Asp Ser Ala Val
                100                 105                 110

Tyr Tyr Cys Ala Lys Gly Gly Trp Phe Ser Met Asp Tyr Trp Gly Gln
                115                 120                 125

Gly Thr Ser Val Thr Val Ser Ser
            130                 135
```

<210> SEQ ID NO 7
<211> LENGTH: 136
<212> TYPE: PRT
<213> ORGANISM: Artificial sequence
<220> FEATURE:
<223> OTHER INFORMATION: Laboratory synthesis

<400> SEQUENCE: 7

```
Met Glu Trp Ser Trp Val Phe Leu Phe Leu Leu Ser Val Ile Ala Gly
 1               5                  10                  15

Val Gln Ser Gln Val Gln Leu Gln Gln Ser Gly Ala Glu Leu Val Arg
                 20                  25                  30

Pro Gly Ala Ser Val Thr Leu Ser Cys Lys Ala Ser Gly Tyr Thr Phe
                 35                  40                  45

Thr Asp Tyr Glu Met His Trp Val Lys Gln Thr Pro Val His Gly Leu
         50                  55                  60

Glu Trp Ile Gly Ala Ile Asp Pro Glu Thr Gly Gly Thr Ala Tyr Asn
 65                  70                  75                  80

Gln Lys Phe Lys Gly Lys Ala Thr Leu Thr Ala Asp Lys Ser Ser Ser
                 85                  90                  95

Thr Ala Tyr Met Glu Leu Arg Ser Leu Thr Ser Glu Asp Ser Ala Val
                100                 105                 110

Tyr Tyr Cys Thr Arg Gly Thr Pro Tyr Ala Met Asp Tyr Trp Gly Gln
                115                 120                 125

Gly Thr Ser Val Thr Val Ser Ser
            130                 135
```

<210> SEQ ID NO 8
<211> LENGTH: 131
<212> TYPE: PRT
<213> ORGANISM: Artificial sequence
<220> FEATURE:
<223> OTHER INFORMATION: Laboratory synthesis

<400> SEQUENCE: 8

```
Met Lys Leu Pro Val Arg Leu Leu Val Leu Met Phe Trp Ile Pro Ala
 1               5                  10                  15

Ser Ser Ser Asp Val Val Met Thr Gln Thr Pro Leu Ser Leu Pro Val
                 20                  25                  30
```

Ser Leu Gly Asp Gln Ala Ser Ile Ser Cys Arg Ser Ser Gln Ser Leu
                35                  40                  45

Val His Ser Asn Gly Asn Thr Tyr Leu His Trp Tyr Leu Gln Lys Pro
 50                  55                  60

Gly Gln Ser Pro Lys Leu Leu Ile Tyr Lys Val Ser Asn Arg Phe Ser
 65                  70                  75                  80

Gly Val Pro Asp Arg Phe Ser Gly Ser Gly Ser Gly Thr Asp Phe Thr
                 85                  90                  95

Leu Lys Ile Ser Arg Val Glu Ala Glu Asp Leu Gly Val Tyr Phe Cys
                100                 105                 110

Ser Gln Ser Thr His Val Pro Trp Thr Phe Gly Gly Gly Thr Lys Leu
            115                 120                 125

Glu Ile Lys
        130

<210> SEQ ID NO 9
<211> LENGTH: 130
<212> TYPE: PRT
<213> ORGANISM: Artificial sequence
<220> FEATURE:
<223> OTHER INFORMATION: Laboratory synthesis

<400> SEQUENCE: 9

Met Lys Leu Pro Val Arg Leu Leu Val Leu Met Phe Trp Ile Pro Ala
1               5                   10                  15

Ser Ser Ser Asp Val Val Met Thr Gln Thr Pro Leu Ser Leu Pro Val
            20                  25                  30

Ser Leu Gly Asp Gln Ala Ser Ile Ser Cys Arg Ser Ser Gln Ser Leu
                35                  40                  45

Val His Ser Asn Gly Lys Thr Tyr Leu Gln Trp Tyr Leu Gln Lys Pro
 50                  55                  60

Gly Gln Ser Pro Lys Leu Leu Ile Tyr Lys Val Ser Asn Arg Phe Ser
 65                  70                  75                  80

Gly Val Pro Asp Arg Phe Ser Gly Ser Gly Ser Gly Thr Asp Phe Thr
                 85                  90                  95

Leu Lys Ile Ser Arg Val Glu Ala Glu Asp Leu Gly Val Tyr Phe Cys
                100                 105                 110

Ser Gln Ser Thr His Val Tyr Thr Phe Gly Gly Gly Thr Lys Leu Glu
            115                 120                 125

Ile Lys
    130

<210> SEQ ID NO 10
<211> LENGTH: 131
<212> TYPE: PRT
<213> ORGANISM: Artificial sequence
<220> FEATURE:
<223> OTHER INFORMATION: Laboratory synthesis

<400> SEQUENCE: 10

Met Lys Leu Pro Val Arg Leu Leu Val Leu Met Phe Trp Ile Pro Ala
1               5                   10                  15

Ser Ser Ser Asp Val Val Met Thr Gln Thr Pro Leu Ser Leu Pro Val
            20                  25                  30

Ser Leu Gly Asp Gln Ala Ser Ile Ser Cys Arg Ser Ser Gln Ser Leu
                35                  40                  45

Val His Ser Lys Gly Asn Thr Tyr Leu His Trp Tyr Leu Gln Lys Pro
 50                  55                  60

```
Gly Gln Ser Pro Lys Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Val Tyr Phe Cys
            100                 105                 110

Ser Gln Ser Thr His Val Pro Phe Thr Phe Gly Ser Gly Thr Lys Leu
        115                 120                 125

Glu Ile Lys
    130

<210> SEQ ID NO 11
<211> LENGTH: 131
<212> TYPE: PRT
<213> ORGANISM: Artificial sequence
<220> FEATURE:
<223> OTHER INFORMATION: Laboratory synthesis

<400> SEQUENCE: 11

Met Lys Leu Pro Val Arg Leu Leu Val Leu Met Phe Trp Ile Pro Ala
1               5                   10                  15

Ser Ser Ser Asp Val Val Met Thr Gln Thr Pro Leu Ser Leu Pro Val
            20                  25                  30

Ser Leu Gly Asp Gln Ala Ser Ile Ser Cys Arg Ser Gln Ser Leu
        35                  40                  45

Val His Ser Asn Gly Asn Thr Tyr Leu His Trp Tyr Leu Gln Lys Pro
    50                  55                  60

Gly Gln Ser Pro Lys Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Val Tyr Phe Cys
            100                 105                 110

Ser Gln Ser Thr His Val Pro Trp Thr Phe Gly Gly Gly Thr Lys Leu
        115                 120                 125

Glu Ile Lys
    130

<210> SEQ ID NO 12
<211> LENGTH: 131
<212> TYPE: PRT
<213> ORGANISM: Artificial sequence
<220> FEATURE:
<223> OTHER INFORMATION: Laboratory synthesis

<400> SEQUENCE: 12

Met Lys Leu Pro Val Arg Leu Leu Val Leu Met Phe Trp Ile Pro Ala
1               5                   10                  15

Ser Ser Ser Asp Val Val Met Thr Gln Thr Pro Leu Ser Leu Pro Val
            20                  25                  30

Ser Leu Gly Asp Gln Ala Ser Ile Ser Cys Arg Ser Gln Ser Leu
        35                  40                  45

Val His Ser Lys Gly Asn Thr Tyr Leu His Trp Tyr Leu Gln Lys Pro
    50                  55                  60

Gly Gln Ser Pro Lys Leu Leu Ile Tyr Arg Val Ser Asn Arg Phe Ser
65                  70                  75                  80

Gly Val Pro Asp Arg Phe Ser Gly Ser Gly Ser Gly Thr Asp Phe Thr
```

```
                85                  90                  95
Leu Lys Ile Ser Arg Val Glu Ala Glu Asp Leu Gly Val Tyr Phe Cys
            100                 105                 110
Ser Gln Ser Thr His Val Pro Phe Thr Phe Gly Ser Gly Thr Lys Leu
        115                 120                 125
Glu Ile Lys
    130

<210> SEQ ID NO 13
<211> LENGTH: 130
<212> TYPE: PRT
<213> ORGANISM: Artificial sequence
<220> FEATURE:
<223> OTHER INFORMATION: Laboratory synthesis

<400> SEQUENCE: 13

Met Lys Leu Pro Val Arg Leu Leu Val Leu Met Phe Trp Ile Pro Ala
1               5                   10                  15
Ser Ser Ser Asp Val Val Met Thr Gln Thr Pro Leu Ser Leu Pro Val
            20                  25                  30
Ser Leu Gly Asp Gln Ala Ser Ile Ser Cys Arg Ser Ser Gln Ser Leu
        35                  40                  45
Val His Ser Asn Gly Lys Thr Tyr Leu Gln Trp Tyr Leu Gln Lys Pro
    50                  55                  60
Gly Gln Ser Pro Lys Leu Leu Ile Tyr Lys Val Ser Asn Arg Phe Ser
65                  70                  75                  80
Gly Val Pro Asp Arg Phe Ser Gly Ser Gly Ser Gly Thr Asp Phe Thr
                85                  90                  95
Leu Lys Ile Ser Arg Val Glu Ala Glu Asp Leu Gly Val Tyr Phe Cys
            100                 105                 110
Ser Gln Ser Thr His Val Tyr Thr Phe Gly Gly Gly Thr Lys Leu Glu
        115                 120                 125
Ile Lys
    130

<210> SEQ ID NO 14
<211> LENGTH: 131
<212> TYPE: PRT
<213> ORGANISM: Artificial sequence
<220> FEATURE:
<223> OTHER INFORMATION: Laboratory synthesis

<400> SEQUENCE: 14

Met Lys Leu Pro Val Arg Leu Leu Val Leu Met Phe Trp Ile Pro Ala
1               5                   10                  15
Ser Ser Ser Asp Val Val Met Thr Gln Thr Pro Leu Ser Leu Pro Val
            20                  25                  30
Ser Leu Gly Asp Gln Ala Ser Ile Ser Cys Arg Ser Ser Gln Ser Leu
        35                  40                  45
Val His Ser Asn Gly Asn Thr Tyr Leu His Trp Tyr Leu Gln Lys Pro
    50                  55                  60
Gly Gln Ser Pro Lys Leu Leu Ile Tyr Lys Val Ser Asn Arg Phe Ser
65                  70                  75                  80
Gly Val Pro Glu Arg Phe Ser Gly Ser Gly Ser Gly Thr Asp Phe Thr
                85                  90                  95
Leu Lys Ile Ser Arg Val Glu Ala Glu Asp Leu Gly Val Tyr Phe Cys
            100                 105                 110
```

Ser Gln Ser Thr His Val Pro Trp Thr Phe Gly Gly Gly Thr Lys Leu
    115                 120                 125

Glu Ile Lys
    130

<210> SEQ ID NO 15
<211> LENGTH: 408
<212> TYPE: DNA
<213> ORGANISM: Artificial sequence
<220> FEATURE:
<223> OTHER INFORMATION: Laboratory synthesis

<400> SEQUENCE: 15
atggaatgga gctgggtctt tctcttcctc ctgtcagtaa ttgcaggtgt ccaatcccag      60
gttcaactgc agcagtctgg ggctgagctg gtgaggcctg gggcttcagt gacgctgtcc     120
tgcaaggctt cgggctacac atttactgac atgaaatgca ctgggtgaa gcagacacct      180 gtgcatggcc tggaatggat tggagctatt gatcctgaaa ctggtggtac tgcctacaat     240
cagaacttca aggcaaggc cacactgact gcagacaaat cctccagcac agcctacatg      300
gagctccgca gcctgacatc tgaggactct gccgtctatt actgtacaag aggtaccccc     360
tatgctatgg actactgggg tcaaggaacc tcagtcaccg tctcctca               408

<210> SEQ ID NO 16
<211> LENGTH: 408
<212> TYPE: DNA
<213> ORGANISM: Artificial sequence
<220> FEATURE:
<223> OTHER INFORMATION: Laboratory synthesis

<400> SEQUENCE: 16
atggaatgga gttggatatt tctctttctc ctgtcaggaa ctgcaggtgt ccactctgag      60
gtccagctgc agcagtctgg acctgagctg gtaaagcctg gggcttcagt gaagatgtcc     120
tgcaaggctt ctggatacac attcactaac tatgttatgc actgggtgaa gcagaagcct     180
ggacagggcc ttgagtggat tggatatatt aatccttaca atgatggtac taactacaat     240
gagaagttca aggcaaggc cacactgact tcagacaaat cctccagcac agcctacatg      300
gagctcagca gcctgacctc tgaggactct gcggtctatt actgtgcaaa aggggggtgg     360
ttctccatgg actactgggg tcaaggaacc tcagtcaccg tctcctca               408

<210> SEQ ID NO 17
<211> LENGTH: 408
<212> TYPE: DNA
<213> ORGANISM: Artificial sequence
<220> FEATURE:
<223> OTHER INFORMATION: Laboratory synthesis

<400> SEQUENCE: 17
atggaatgga gttggatatt tctctttctc ctgtcaggaa ctgcaggtgt ccactctgag      60
gtccagctgc agcagtctgg acctgagctg gtaaagcctg gggcttcagt gaagatgtcc     120
tgcaaggctt ctggatacac attcactaac tatgttatgc actggatgaa gcagaagcct     180
gggcagggcc ttgagtggat tggatatatt aatccttaca atgatgatac taaatacaat     240
gagaaattca aggacagggc cacactgact tcagacaaat cctccagcac agcctacatg     300
gagctcagca gcctgacctc tgaggactct gcggtctatt actgtgcaaa ggggggttac     360
tattctatgg actactgggg tcaaggaacc tcagtcaccg tctcctca               408

<210> SEQ ID NO 18
<211> LENGTH: 408
<212> TYPE: DNA
<213> ORGANISM: Artificial sequence
<220> FEATURE:
<223> OTHER INFORMATION: Laboratory synthesis

<400> SEQUENCE: 18

| atggaatgga gctgggtctt tctcttcctc ctgtcagtaa ttgcaggtgt ccaatcccag | 60 |
| gttcaactgc agcagtctgg ggctgagctg gtgaggcctg ggcttcagt gacgctgtcc | 120 |
| tgcaaggctt cgggctacac atttactgac tatgaaatgc actgggtgaa gcagacacct | 180 |
| gtgcatggcc tggaatggat tggagctatt gatcctgaaa ctggtggtac tgcctacaat | 240 |
| cagaagttca aggcaaggc cacactgact gcagacaaat cctccagcac agcctacatg | 300 |
| gaactccgca gcctgacatc tgaggactct gccgtctatt actgtacaag aggtaccccc | 360 |
| tatgctatgg actactgggg tcaaggaacc tcagtcaccg tctcctca | 408 |

<210> SEQ ID NO 19
<211> LENGTH: 408
<212> TYPE: DNA
<213> ORGANISM: Artificial sequence
<220> FEATURE:
<223> OTHER INFORMATION: Laboratory synthesis

<400> SEQUENCE: 19

| atggaatgga gttggatatt tctctttctc ctgtcaggaa ctgcaggtgt ccactctgag | 60 |
| gtccagctgc agcagtctgg acctgagctg gtaaagcctg ggcttcagt gaggatgtcc | 120 |
| tgcaaggctt ctggatacac attcactaac tatgttatgc actgggtgaa gcagaagcct | 180 |
| ggcagggac ttgagtggat tggatatatt aatccttaca atgatggtac taagtacagt | 240 |
| gagaagttca aggcaaggc cacactgact tcagacaaat cctccatcac agcctatatg | 300 |
| gagctcagca gcctgacctc tgaggactct gcggtctatt actgtgcaaa aggggggctt | 360 |
| tttacctttg actactgggg ccaaggcacc actctcacag tctcctca | 408 |

<210> SEQ ID NO 20
<211> LENGTH: 408
<212> TYPE: DNA
<213> ORGANISM: Artificial sequence
<220> FEATURE:
<223> OTHER INFORMATION: Laboratory synthesis

<400> SEQUENCE: 20

| atggaatgga gttggatatt tctctttctc ctgtcaggaa ctgcaggtgt ccactctgag | 60 |
| gtccagctgc agcagtctgg acctgagctg gtaaagcctg ggcttcagt taatatgtcc | 120 |
| tgcaaggctt ctggatacac attcactaac tattttttgc actgggtgaa gcagaagcct | 180 |
| ggcagggcc ttgagtggat tggatatatt aatccttaca atgatggtac taactacaat | 240 |
| gagaacttca aggcaaggc cactctgact tcagacaaat cctccagcac agcctacatg | 300 |
| gagctcagca gcctgacctc tgaggactct gcggtctatt actgtgcaaa agggggtgg | 360 |
| ttctccatgg actactgggg tcaaggaacc tcagtcaccg tctcctca | 408 |

<210> SEQ ID NO 21
<211> LENGTH: 408
<212> TYPE: DNA
<213> ORGANISM: Artificial sequence
<220> FEATURE:
<223> OTHER INFORMATION: Laboratory synthesis

<400> SEQUENCE: 21

```
atggaatgga gctgggtctt tctcttcctc ctgtcagtaa ttgcaggtgt ccaatcccag    60
gttcaactgc agcagtctgg ggctgagctg gtgaggcctg ggcttcagt gacgctgtcc    120
tgcaaggctt cgggctacac atttactgac tatgaaatgc actgggtgaa gcagacacct    180
gtgcatggcc tggaatggat tggagctatt gatcctgaaa ctggtggtac tgcctacaat    240
cagaagttca gggcaaggc cacactgact gcagacaaat cctccagcac agcctacatg    300
gagctccgca gcctgacatc tgaggactct gccgtctatt actgtacaag aggtaccccc    360
tatgctatgg actactgggg tcaaggaacc tcagtcaccg tctcctca                408
```

<210> SEQ ID NO 22
<211> LENGTH: 393
<212> TYPE: DNA
<213> ORGANISM: Artificial sequence
<220> FEATURE:
<223> OTHER INFORMATION: Laboratory synthesis

<400> SEQUENCE: 22

```
atgaagttgc ctgttaggct gttggtgctg atgttctgga ttcctgcttc cagcagtgat    60
gttgtgatga cccaaactcc actctccctg cctgtcagtc ttggagatca agcctccatc    120
tcttgcagat ctagtcagag ccttgtacac agtaatggaa acacctattt acattggtac    180
ctgcagaagc caggccagtc tccaaagctc ctgatctaca agtttccaa ccgattttct    240
ggggtcccag acaggttcag tggcagtgga tcagggacag atttcacact caagatcagc    300
agagtggagg ctgaggatct gggagtttat ttctgctctc aaagtacaca tgttccgtgg    360
acgttcggtg gaggcaccaa gctggaaatc aaa                                393
```

<210> SEQ ID NO 23
<211> LENGTH: 390
<212> TYPE: DNA
<213> ORGANISM: Artificial sequence
<220> FEATURE:
<223> OTHER INFORMATION: Laboratory synthesis

<400> SEQUENCE: 23

```
atgaagttgc ctgttaggct gttggtgctg atgttctgga ttcctgcttc cagcagtgat    60
gttgtgatga cccaaactcc actctccctg cctgtcagtc ttggagatca agcctccatc    120
tcttgcagat ctagtcagag ccttgtacac agtaatggaa aaacctattt acagtggtac    180
ctgcagaagc caggccagtc tccaaagctc ctgatctaca agtttccaa ccgattttct    240
ggggtcccag acaggttcag tggcagtgga tcagggacag atttcacact caagatcagc    300
agagtggagg ctgaggatct gggagtttat ttctgctctc aaagtacaca tgtttacacg    360
ttcggagggg ggaccaagct ggaaataaaa                                    390
```

<210> SEQ ID NO 24
<211> LENGTH: 393
<212> TYPE: DNA
<213> ORGANISM: Artificial sequence
<220> FEATURE:
<223> OTHER INFORMATION: Laboratory synthesis

<400> SEQUENCE: 24

```
atgaagttgc ctgttaggct gttggtgctg atgttctgga ttcctgcttc cagcagtgat    60
gttgtgatga cccaaactcc actttctctg cctgtcagtc ttggagatca agcctccatc    120
tcttgcagat ctagtcagag ccttgtacac agtaaaggaa acacctattt acattggtac    180
```

```
ctgcagaagc caggccagtc tccaaagctc ctgatctaca aagtttccaa ccgattttct    240
ggggtcccag acaggttcag tggcagtgga tcagggacag atttcacact caagatcagc    300
agagtggagg ctgaggatct gggagtttat ttctgctctc aaagtacaca tgttccattc    360
acgttcggct cggggacaaa gttggaaata aaa                                  393
```

<210> SEQ ID NO 25
<211> LENGTH: 393
<212> TYPE: DNA
<213> ORGANISM: Artificial sequence
<220> FEATURE:
<223> OTHER INFORMATION: Laboratory synthesis

<400> SEQUENCE: 25

```
atgaagttgc ctgttaggct gttggtgctg atgttctgga ttcctgcttc cagcagtgat     60
gttgtgatga cccaaactcc actctccctg cctgtcagtc ttggagatca agcctccatc    120
tcttgcagat ctagtcagag ccttgtacac agtaatggaa acacctattt acattggtac    180
ctgcagaagc caggccagtc tccaaagctc ctgatctaca aagtttccaa ccgattttct    240
ggggtcccag acaggttcag tggcagtgga tcagggacag atttcacact caagatcagc    300
agagtggagg ctgaggatct gggagtttat ttctgctctc aaagtacaca tgttccgtgg    360
acgttcggtg gaggcaccaa gctggaaatc aaa                                  393
```

<210> SEQ ID NO 26
<211> LENGTH: 393
<212> TYPE: DNA
<213> ORGANISM: Artificial sequence
<220> FEATURE:
<223> OTHER INFORMATION: Laboratory synthesis

<400> SEQUENCE: 26

```
atgaagttgc ctgttaggct gttggtgctg atgttctgga ttcctgcttc cagcagtgat     60
gttgtgatga cccaaactcc actctccctg cctgtcagcc ttggagatca agcctccatc    120
tcttgcagat ctagtcagag ccttgtacac agtaaaggaa acacctattt acattggtac    180
ctgcagaagc caggccagtc tccaaagctc ctgatctaca gagtgtccaa ccgattttct    240
ggggtcccag acaggttcag tggcagtgga tcagggacag atttcacact caagatcagc    300
agagtggagg ctgaggatct gggagtttat ttctgctctc aaagtacaca tgttccattc    360
acgttcggct cggggacaaa gttggaaata aaa                                  393
```

<210> SEQ ID NO 27
<211> LENGTH: 390
<212> TYPE: DNA
<213> ORGANISM: Artificial sequence
<220> FEATURE:
<223> OTHER INFORMATION: Laboratory synthesis

<400> SEQUENCE: 27

```
atgaagttgc ctgttaggct gttggtgctg atgttctgga ttcctgcttc cagcagtgat     60
gttgtgatga cccaaactcc actctccctg cctgtcagtc ttggagatca agcctccatc    120
tcttgcagat ctagtcagag ccttgtacac agtaatggaa aaacctattt acagtggtac    180
ctgcagaagc caggccagtc tccaaagctc ctgatctaca aagtttccaa ccgattttct    240
ggggtcccag acaggttcag tggcagtgga tcagggacag atttcacact caagatcagc    300
agagtggagg ctgaggatct gggagtttat ttctgctctc aaagtacaca tgtttacacg    360
```

-continued

```
ttcggaggggg ggaccaagct ggaaataaaa                               390
```

<210> SEQ ID NO 28
<211> LENGTH: 393
<212> TYPE: DNA
<213> ORGANISM: Artificial sequence
<220> FEATURE:
<223> OTHER INFORMATION: Laboratory synthesis

<400> SEQUENCE: 28

```
atgaagttgc ctgttaggct gttggtgctg atgttctgga ttcctgcttc cagcagtgat    60
gttgtgatga cccaaactcc actctccctg cctgtcagtc ttggagatca agcctccatc   120
tcttgcagat ctagtcagag ccttgtacac agtaatggaa acacctattt acattggtac   180
ctgcagaagc caggccagtc tccaaagctc ctgatctaca agtttccaa ccgattttct    240
ggggtcccag aaaggttcag tggcagtgga tcaggacag atttcacact caagatcagc    300
agagtggagg ctgaggatct gggagtttat ttctgctctc aaagtacaca tgttccgtgg   360
acgttcggtg aggcaccaa gctggaaatc aaa                                 393
```

<210> SEQ ID NO 29
<211> LENGTH: 379
<212> TYPE: PRT
<213> ORGANISM: Artificial sequence
<220> FEATURE:
<223> OTHER INFORMATION: Laboratory synthesis

<400> SEQUENCE: 29

```
Met Trp Pro Leu Val Ala Ala Leu Leu Leu Gly Ser Ala Cys Cys Gly
1               5                   10                  15
Ser Ala Gln Leu Leu Phe Asn Lys Thr Lys Ser Val Glu Phe Thr Phe
            20                  25                  30
Cys Asn Asp Thr Val Val Ile Pro Cys Phe Val Thr Asn Met Glu Ala
        35                  40                  45
Gln Asn Thr Thr Glu Val Tyr Val Lys Trp Lys Phe Lys Gly Arg Asp
    50                  55                  60
Ile Tyr Thr Phe Asp Gly Ala Leu Asn Lys Ser Thr Val Pro Thr Asp
65                  70                  75                  80
Phe Ser Ser Ala Lys Ile Glu Val Ser Gln Leu Leu Lys Gly Asp Ala
                85                  90                  95
Ser Leu Lys Met Asp Lys Ser Asp Ala Val Ser His Thr Gly Asn Tyr
            100                 105                 110
Thr Cys Glu Val Thr Glu Leu Thr Arg Glu Gly Glu Thr Ile Ile Glu
        115                 120                 125
Leu Lys Tyr Arg Val Val Ser Trp Phe Ser Pro Ser Gly Gly Gly Gly
    130                 135                 140
Ser Ala Ser Glu Pro Lys Ser Cys Asp Lys Thr His Thr Cys Pro Pro
145                 150                 155                 160
Cys Pro Ala Pro Glu Leu Leu Gly Gly Pro Ser Val Phe Leu Phe Pro
                165                 170                 175
Pro Lys Pro Lys Asp Thr Leu Met Ile Ser Arg Thr Pro Glu Val Thr
            180                 185                 190
Cys Val Val Val Asp Val Ser His Glu Asp Pro Glu Val Lys Phe Asn
        195                 200                 205
Trp Tyr Val Asp Gly Val Glu Val His Asn Ala Lys Thr Lys Pro Arg
    210                 215                 220
Glu Glu Gln Tyr Asn Ser Thr Tyr Arg Val Val Ser Val Leu Thr Val
```

```
                225                 230                 235                 240
Leu His Gln Asp Trp Leu Asn Gly Lys Glu Tyr Lys Cys Lys Val Ser
                245                 250                 255

Asn Lys Ala Leu Pro Ala Pro Ile Glu Lys Thr Ile Ser Lys Ala Lys
            260                 265                 270

Gly Gln Pro Arg Glu Pro Gln Val Tyr Thr Leu Pro Pro Ser Arg Asp
        275                 280                 285

Glu Leu Thr Lys Asn Gln Val Ser Leu Thr Cys Leu Val Lys Gly Phe
    290                 295                 300

Tyr Pro Ser Asp Ile Ala Val Glu Trp Glu Ser Asn Gly Gln Pro Glu
305                 310                 315                 320

Asn Asn Tyr Lys Thr Thr Pro Pro Val Leu Asp Ser Asp Gly Ser Phe
                325                 330                 335

Phe Leu Tyr Ser Lys Leu Thr Val Asp Lys Ser Arg Trp Gln Gln Gly
            340                 345                 350

Asn Val Phe Ser Cys Ser Val Met His Glu Ala Leu His Asn His Tyr
        355                 360                 365

Thr Gln Lys Ser Leu Ser Leu Ser Pro Gly Lys
    370                 375

<210> SEQ ID NO 30
<211> LENGTH: 152
<212> TYPE: PRT
<213> ORGANISM: Artificial sequence
<220> FEATURE:
<223> OTHER INFORMATION: Laboratory synthesis

<400> SEQUENCE: 30

Met Trp Pro Leu Val Ala Ala Leu Leu Leu Gly Ser Ala Cys Cys Gly
1               5                   10                  15

Ser Ala Gln Leu Leu Phe Asn Lys Thr Lys Ser Val Glu Phe Thr Phe
            20                  25                  30

Cys Asn Asp Thr Val Val Ile Pro Cys Phe Val Thr Asn Met Glu Ala
        35                  40                  45

Gln Asn Thr Thr Glu Val Tyr Val Lys Trp Lys Phe Lys Gly Arg Asp
    50                  55                  60

Ile Tyr Thr Phe Asp Gly Ala Leu Asn Lys Ser Thr Val Pro Thr Asp
65                  70                  75                  80

Phe Ser Ser Ala Lys Ile Glu Val Ser Gln Leu Leu Lys Gly Asp Ala
                85                  90                  95

Ser Leu Lys Met Asp Lys Ser Asp Ala Val Ser His Thr Gly Asn Tyr
            100                 105                 110

Thr Cys Glu Val Thr Glu Leu Thr Arg Glu Gly Glu Thr Ile Ile Glu
        115                 120                 125

Leu Lys Tyr Arg Val Val Ser Trp Phe Ser Pro Ser Gly Gly Gly Gly
    130                 135                 140

Ser His His His His His His
145                 150

<210> SEQ ID NO 31
<211> LENGTH: 379
<212> TYPE: PRT
<213> ORGANISM: Artificial sequence
<220> FEATURE:
<223> OTHER INFORMATION: Laboratory synthesis

<400> SEQUENCE: 31
```

```
Met Trp Pro Leu Val Ala Ala Leu Leu Gly Ser Ala Cys Cys Gly
1               5                   10                  15

Ser Ala Gln Leu Leu Phe Asn Lys Thr Lys Ser Val Glu Phe Thr Phe
            20                  25                  30

Cys Asn Asp Thr Val Val Ile Pro Cys Phe Val Thr Asn Met Glu Ala
            35                  40                  45

Gln Asn Thr Thr Glu Val Tyr Val Lys Trp Lys Phe Lys Gly Arg Asp
50                  55                  60

Ile Tyr Thr Phe Asp Gly Ala Leu Asn Lys Ser Thr Ala Pro Ala Asn
65                  70                  75                  80

Phe Ser Ser Ala Lys Ile Glu Val Ser Gln Leu Leu Lys Gly Asp Ala
                85                  90                  95

Ser Leu Lys Met Asp Lys Ser Asp Ala Val Ser His Thr Gly Asn Tyr
            100                 105                 110

Thr Cys Glu Val Thr Glu Leu Thr Arg Glu Gly Glu Thr Ile Ile Glu
            115                 120                 125

Leu Lys Tyr Arg Val Val Ser Trp Phe Ser Pro Ser Gly Gly Gly Gly
            130                 135                 140

Ser Ala Ser Glu Pro Lys Ser Cys Asp Lys Thr His Thr Cys Pro Pro
145                 150                 155                 160

Cys Pro Ala Pro Glu Leu Leu Gly Gly Pro Ser Val Phe Leu Phe Pro
                165                 170                 175

Pro Lys Pro Lys Asp Thr Leu Met Ile Ser Arg Thr Pro Glu Val Thr
            180                 185                 190

Cys Val Val Val Asp Val Ser His Glu Asp Pro Glu Val Lys Phe Asn
            195                 200                 205

Trp Tyr Val Asp Gly Val Glu Val His Asn Ala Lys Thr Lys Pro Arg
210                 215                 220

Glu Glu Gln Tyr Asn Ser Thr Tyr Arg Val Val Ser Val Leu Thr Val
225                 230                 235                 240

Leu His Gln Asp Trp Leu Asn Gly Lys Glu Tyr Lys Cys Lys Val Ser
                245                 250                 255

Asn Lys Ala Leu Pro Ala Pro Ile Glu Lys Thr Ile Ser Lys Ala Lys
            260                 265                 270

Gly Gln Pro Arg Glu Pro Gln Val Tyr Thr Leu Pro Pro Ser Arg Asp
            275                 280                 285

Glu Leu Thr Lys Asn Gln Val Ser Leu Thr Cys Leu Val Lys Gly Phe
            290                 295                 300

Tyr Pro Ser Asp Ile Ala Val Glu Trp Glu Ser Asn Gly Gln Pro Glu
305                 310                 315                 320

Asn Asn Tyr Lys Thr Thr Pro Pro Val Leu Asp Ser Asp Gly Ser Phe
                325                 330                 335

Phe Leu Tyr Ser Lys Leu Thr Val Asp Lys Ser Arg Trp Gln Gln Gly
            340                 345                 350

Asn Val Phe Ser Cys Ser Val Met His Glu Ala Leu His Asn His Tyr
            355                 360                 365

Thr Gln Lys Ser Leu Ser Leu Ser Pro Gly Lys
    370                 375

<210> SEQ ID NO 32
<211> LENGTH: 152
<212> TYPE: PRT
<213> ORGANISM: Artificial sequence
<220> FEATURE:
<223> OTHER INFORMATION: Laboratory synthesis
```

<400> SEQUENCE: 32

| | | | | | | | | | | | | | | |
|---|---|---|---|---|---|---|---|---|---|---|---|---|---|---|
|Met|Trp|Pro|Leu|Val|Ala|Ala|Leu|Leu|Gly|Ser|Ala|Cys|Cys|Gly|
|1| | | |5| | | | |10| | | | |15|
|Ser|Ala|Gln|Leu|Leu|Phe|Asn|Lys|Thr|Lys|Ser|Val|Glu|Phe|Thr|Phe|
| | | |20| | | | |25| | | | |30| | |
|Cys|Asn|Asp|Thr|Val|Val|Ile|Pro|Cys|Phe|Val|Thr|Asn|Met|Glu|Ala|
| | | |35| | | | |40| | | | |45| | |
|Gln|Asn|Thr|Thr|Glu|Val|Tyr|Val|Lys|Trp|Lys|Phe|Lys|Gly|Arg|Asp|
| |50| | | | |55| | | | |60| | | | |
|Ile|Tyr|Thr|Phe|Asp|Gly|Ala|Leu|Asn|Lys|Ser|Thr|Ala|Pro|Ala|Asn|
|65| | | | |70| | | | |75| | | | |80|
|Phe|Ser|Ser|Ala|Lys|Ile|Glu|Val|Ser|Gln|Leu|Leu|Lys|Gly|Asp|Ala|
| | | | |85| | | | |90| | | | |95| |
|Ser|Leu|Lys|Met|Asp|Lys|Ser|Asp|Ala|Val|Ser|His|Thr|Gly|Asn|Tyr|
| | | | |100| | | | |105| | | | |110| |
|Thr|Cys|Glu|Val|Thr|Glu|Leu|Thr|Arg|Glu|Gly|Glu|Thr|Ile|Ile|Glu|
| | | | |115| | | | |120| | | | |125| |
|Leu|Lys|Tyr|Arg|Val|Val|Ser|Trp|Phe|Ser|Pro|Ser|Gly|Gly|Gly|Gly|
| |130| | | | |135| | | | |140| | | | |
|Ser|His|His|His|His|His|His| | | | | | | | | |
|145| | | |150| | | | | | | | | | | |

<210> SEQ ID NO 33
<211> LENGTH: 1137
<212> TYPE: DNA
<213> ORGANISM: Artificial sequence
<220> FEATURE:
<223> OTHER INFORMATION: Laboratory synthesis

<400> SEQUENCE: 33

```
atgtggcccc tggtagcggc gctgttgctg ggctcggcgt gctgcggatc agctcagcta      60
ctatttaata aacaaaatc tgtagaattc acgttttgta atgacactgt cgtcattcca     120
tgctttgtta ctaatatgga ggcacaaaac actactgaag tatacgtaaa gtggaaattt     180
aaaggaagag atatttacac ctttgatgga gctctaaaca gtccactgt ccccactgac     240
tttagtagtg caaaaattga agtctcacaa ttactaaaag gagatgcctc tttgaagatg     300
gataagagtg atgctgtctc acacacagga actacactt gtgaagtaac agaattaacc     360
agagaaggtg aaacgatcat cgagctaaaa tatcgtgttg tttcatggtt ttctccatcc     420
ggaggtggag gttccgctag cgagcccaaa tcttgtgaca aaactcacac atgcccaccg     480
tgcccagcac ctgaactcct ggggggaccg tcagtcttcc tcttcccccc aaaacccaag     540
gacaccctca tgatctcccg gacccctgag gtcacatgcg tggtggtgga cgtgagccac     600
gaagaccctg aggtcaagtt caactggtac gtggacggcg tggaggtgca taatgccaag     660
acaaagccgc gggaggagca gtacaacagc acgtaccgtg tggtcagcgt cctcaccgtc     720
ctgcaccagg actggctgaa tggcaaggag tacaagtgca aggtctccaa caaagccctc     780
ccagccccca tcgagaaaac catctccaaa gccaaagggc agccccgaga accacaggtg     840
tacaccctgc ctccatctcg ggatgagctg accaagaacc aggtcagcct gacctgcctg     900
gtcaaaggct tctatcccag cgacatcgcc gtggagtggg agagcaatgg gcagccggag     960
aacaactaca agaccacgcc tcccgtgctg gactccgacg gctccttctt cctctatagc    1020
aagctcaccg tggacaagag caggtggcag caggggaacg tcttctcatg ctccgtgatg    1080
```
catgaggctc tgcacaacca ctacacgcag aagagcctct ccctgtctcc gggtaaa    1137

<210> SEQ ID NO 34
<211> LENGTH: 457
<212> TYPE: DNA
<213> ORGANISM: Artificial sequence
<220> FEATURE:
<223> OTHER INFORMATION: Laboratory synthesis

<400> SEQUENCE: 34
atgtggcccc tggtagcggc gctgttgctg ggctcggcgt gctgcggatc agctcagcta    60
ctatttaata aaacaaaatc tgtagaattc acgttttgta atgacactgt cgtcattcca   120
tgctttgtta ctaatatgga ggcacaaaac actactgaag tatacgtaaa gtggaaattt   180
aaaggaagag atatttacac ctttgatgga gctctaaaca gtccactgt ccccactgac   240
tttagtagtg caaaaattga gtctcacaa ttactaaaag gagatgcctc tttgaagatg   300
gataagagtg atgctgtctc acacacagga aactacactt gtgaagtaac agaattaacc   360
agagaaggtg aaacgatcat cgagctaaaa tatcgtgttg tttcatggtt ttctccatcc   420
ggaggtggtg gatcccatca ccatcaccac catcatt                           457

<210> SEQ ID NO 35
<211> LENGTH: 1137
<212> TYPE: DNA
<213> ORGANISM: Artificial sequence
<220> FEATURE:
<223> OTHER INFORMATION: Laboratory synthesis

<400> SEQUENCE: 35
atgtggcccc tggtagcggc gctgttgctg ggctcggcgt gctgcggatc agctcaacta    60
ctatttaata aaacaaaatc tgtagaattc acgttctgta atgacactgt cgtcattcca   120
tgctttgtta ctaatatgga ggcacaaaac actaccgaag tatatgtaaa gtggaaattt   180
aaaggaagag atatttacac gtttgatgga gctctaaaca gtccactgc cccgctaac    240
tttagtagtg caaaaattga gtctcacaa ttactaaaag gagatgcctc tttgaagatg   300
gataagagtg atgctgtctc acacacagga aactacactt gtgaagtaac agaattaacc   360
agagaaggtg aaacgatcat tgagctaaaa tatcgtgttg tttcgtggtt ttctccatcc   420
ggaggtggag gttccgctag cgagcccaaa tcttgtgaca aaactcacac atgcccaccg   480
tgcccagcac ctgaactcct ggggggaccg tcagtcttcc tcttcccccc aaaacccaag   540
gacaccctca tgatctcccg gacccctgag gtcacatgcg tggtggtgga cgtgagccac   600
gaagaccctg aggtcaagtt caactggtac gtggacggcg tggaggtgca taatgccaag   660
acaaagccgc gggaggagca gtacaacagc acgtaccgtg tggtcagcgt cctcaccgtc   720
ctgcaccagg actggctgaa tggcaaggag tacaagtgca aggtctccaa caaagccctc   780
ccagccccca tcgagaaaac catctccaaa gccaaagggc agccccgaga accacaggtg   840
tacaccctgc ctccatctcg ggatgagctg accaagaacc aggtcagcct gacctgcctg   900
gtcaaaggct tctatcccag cgacatcgcc gtggagtggg agagcaatgg gcagccggag   960
aacaactaca agaccacgcc tcccgtgctg gactccgacg gctccttctt cctctatagc   1020
aagctcaccg tggacaagag caggtggcag caggggaacg tcttctcatg ctccgtgatg   1080
catgaggctc tgcacaacca ctacacgcag aagagcctct ccctgtctcc gggtaaa    1137

<210> SEQ ID NO 36
<211> LENGTH: 457

```
<212> TYPE: DNA
<213> ORGANISM: Artificial sequence
<220> FEATURE:
<223> OTHER INFORMATION: Laboratory synthesis

<400> SEQUENCE: 36
atgtggcccc tggtagcggc gctgttgctg ggctcggcgt gctgcggatc agctcaacta    60
ctatttaata aacaaaatc tgtagaattc acgttctgta atgacactgt cgtcattcca    120
tgctttgtta ctaatatgga ggcacaaaac actaccgaag tatatgtaaa gtggaaattt    180
aaaggaagag atatttacac gtttgatgga gctctaaaca agtccactgc ccccgctaac    240
tttagtagtg caaaaattga agtctcacaa ttactaaaag gagatgcctc tttgaagatg    300
gataagagtg atgctgtctc acacacagga aactacactt gtgaagtaac agaattaacc    360
agagaaggtg aaacgatcat tgagctaaaa tatcgtgttg tttcgtggtt ttctccatcc    420
ggaggtggtg gatcccatca ccatcaccac catcatt                             457

<210> SEQ ID NO 37
<211> LENGTH: 444
<212> TYPE: PRT
<213> ORGANISM: Artificial sequence
<220> FEATURE:
<223> OTHER INFORMATION: Laboratory synthesis

<400> SEQUENCE: 37
```

Gln Val Gln Leu Val Gln Ser Gly Ala Glu Val Lys Lys Pro Gly Ala
1               5                   10                  15

Ser Val Gln Val Ser Cys Lys Ala Ser Gly Tyr Thr Phe Thr Asn His
            20                  25                  30

Val Ile His Trp Leu Arg Gln Ala Pro Gly Gln Gly Leu Glu Trp Met
        35                  40                  45

Gly Tyr Ile Tyr Pro Tyr Asn Asp Gly Thr Lys Tyr Asn Glu Lys Phe
    50                  55                  60

Lys Asp Arg Val Thr Met Thr Ser Asp Thr Ser Ile Ser Thr Ala Tyr
65                  70                  75                  80

Met Glu Leu Ser Ser Leu Arg Ser Asp Asp Thr Ala Val Tyr Tyr Cys
                85                  90                  95

Ala Arg Gly Gly Tyr Tyr Thr Tyr Asp Asp Trp Gly Gln Ala Thr Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Ser Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val

```
                245                 250                 255
Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Lys
        435                 440

<210> SEQ ID NO 38
<211> LENGTH: 1332
<212> TYPE: DNA
<213> ORGANISM: Artificial sequence
<220> FEATURE:
<223> OTHER INFORMATION: Laboratory synthesis

<400> SEQUENCE: 38
caggtgcagc tggtgcagtc tggggctgag gtgaagaagc ctggggcctc agtgcaggtt      60
tcctgtaagg catctggata caccttcacc aaccatgtta ttcactggct gcgacaggcc     120
cctggacaag gcttgagtg gatgggatat atttatcctt acaatgatgg tactaagtat     180
aatgagaagt tcaaggacag agtcacgatg acctcagaca cgtccatcag cacagcctac     240
atggagttga gcagtctcag atctgacgac acggccgtct attattgtgc tagagggggt     300
tactatactt acgacgactg gggccaagca accctggtca ccgtctcgag cgctagcacc     360
aagggcccat ccgtcttccc cctggcgccc tgctccagga gcacctccga gagcacagcc     420
gccctgggct gcctggtcaa ggactacttc cccgaaccgg tgacggtgtc gtggaactca     480
ggcgccctga ccagcggcgt gcacaccttc ccggctgtcc tacagtcctc aggactctac     540
tccctcagca gcgtggtgac cgtgccctcc agcagcttgg gcacgaagac ctacacctgc     600
aacgtagatc acaagcccag caacaccaag gtggacaaga gagttgagtc caaatatggt     660
cccccatgcc caccatgccc agcacctgag ttcctggggg gaccatcagt cttcctgttc     720
cccccaaaac ccaaggacac tctcatgatc tcccggaccc ctgaggtcac gtgcgtggtg     780
gtggacgtga gccaggaaga cccgaggtc cagttcaact ggtacgtgga tggcgtggag     840
gtgcataatg ccaagacaaa gccgcgggag gagcagttca acagcacgta ccgtgtggtc     900
agcgtcctca ccgtcctgca ccaggactgg ctgaacggca aggagtacaa gtgcaaggtc     960
```

```
tccaacaaag gcctcccgtc ctccatcgag aaaaccatct ccaaagccaa agggcagccc    1020
cgagagccac aggtgtacac cctgccccca tcccaggagg agatgaccaa gaaccaggtc    1080
agcctgacct gcctggtcaa aggcttctac cccagcgaca tcgccgtgga gtgggagagc    1140
aatgggcagc cggagaacaa ctacaagacc acgcctcccg tgctggactc cgacggctcc    1200
ttcttcctct acagcaggct aaccgtggac aagagcaggt ggcaggaggg gaatgtcttc    1260
tcatgctccg tgatgcatga ggctctgcac aaccactaca cacagaagag cctctccctg    1320
tctctgggta aa                                                        1332
```

<210> SEQ ID NO 39
<211> LENGTH: 219
<212> TYPE: PRT
<213> ORGANISM: Artificial sequence
<220> FEATURE:
<223> OTHER INFORMATION: Laboratory synthesis

<400> SEQUENCE: 39

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Gly Lys Thr Tyr Leu His Trp Tyr Leu Gln Lys Pro Gly Gln Ser
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Asp Asp Val Gly Ile Tyr Tyr Cys Ser Gln Ser
                85                  90                  95

Thr His Val Pro Tyr Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 40
<211> LENGTH: 657
<212> TYPE: PRT
<213> ORGANISM: Artificial sequence
<220> FEATURE:
<223> OTHER INFORMATION: Laboratory synthesis

<400> SEQUENCE: 40

```
Gly Ala Thr Ala Thr Thr Gly Thr Gly Ala Thr Gly Ala Cys Thr Cys
1               5                   10                  15
```

-continued

```
Ala Gly Thr Cys Thr Cys Cys Ala Cys Thr Cys Thr Cys Cys Cys Thr
            20                  25                  30

Gly Cys Cys Cys Gly Thr Cys Ala Cys Cys Cys Cys Thr Gly Gly Ala
        35                  40                  45

Gly Ala Gly Cys Cys Gly Gly Cys Cys Thr Cys Cys Ala Thr Cys Thr
    50                  55                  60

Cys Cys Thr Gly Cys Ala Gly Ala Thr Cys Ala Ala Gly Thr Cys Ala
65                  70                  75                  80
Gly Ala Gly Cys Cys Thr Thr Gly Thr Gly Cys Ala Cys Ala Gly Thr
                85                  90                  95

Ala Ala Thr Gly Gly Ala Ala Ala Gly Ala Cys Cys Thr Ala Thr Thr
            100                 105                 110

Thr Ala Cys Ala Thr Thr Gly Gly Thr Ala Thr Cys Thr Gly Cys Ala
        115                 120                 125
Gly Ala Ala Gly Cys Cys Ala Gly Gly Cys Cys Ala Gly Thr Cys Thr
    130                 135                 140

Cys Cys Ala Ala Gly Ala Cys Thr Cys Cys Thr Gly Ala Thr Cys Thr
145                 150                 155                 160

Ala Cys Ala Ala Ala Gly Thr Thr Thr Cys Cys Ala Ala Cys Cys Gly
                165                 170                 175

Ala Thr Thr Thr Thr Cys Thr Gly Gly Thr Gly Thr Cys Cys Cys Ala
            180                 185                 190

Gly Ala Cys Ala Gly Ala Thr Thr Cys Ala Gly Cys Gly Gly Cys Ala
        195                 200                 205

Gly Thr Gly Gly Gly Thr Cys Ala Gly Gly Cys Ala Cys Thr Gly Ala
    210                 215                 220

Thr Thr Thr Cys Ala Cys Ala Cys Thr Gly Ala Ala Ala Ala Thr Cys
225                 230                 235                 240

Ala Gly Cys Ala Gly Gly Gly Thr Gly Gly Ala Gly Gly Cys Thr Gly
                245                 250                 255

Ala Thr Gly Ala Thr Gly Thr Thr Gly Gly Ala Ala Thr Thr Thr Ala
            260                 265                 270

Thr Thr Ala Cys Thr Gly Cys Thr Cys Thr Cys Ala Ala Ala Gly Thr
        275                 280                 285

Ala Cys Ala Cys Ala Thr Gly Thr Thr Cys Cys Gly Thr Ala Cys Ala
    290                 295                 300

Cys Gly Thr Thr Thr Gly Gly Cys Cys Ala Gly Gly Gly Gly Ala Cys
305                 310                 315                 320

Cys Ala Ala Gly Cys Thr Gly Gly Ala Gly Ala Thr Cys Ala Ala Ala
                325                 330                 335

Cys Gly Gly Ala Cys Cys Gly Thr Gly Gly Cys Gly Gly Cys Gly Cys
            340                 345                 350

Cys Ala Thr Cys Thr Gly Thr Cys Thr Thr Cys Ala Thr Cys Thr Thr
        355                 360                 365

Cys Cys Cys Gly Cys Cys Ala Thr Cys Thr Gly Ala Thr Gly Ala Gly
    370                 375                 380

Cys Ala Gly Thr Thr Gly Ala Ala Ala Thr Cys Thr Gly Gly Thr Ala
385                 390                 395                 400

Cys Cys Gly Cys Thr Ala Gly Cys Gly Thr Thr Gly Thr Gly Thr Gly
                405                 410                 415

Cys Cys Thr Gly Cys Thr Gly Ala Ala Thr Ala Ala Cys Thr Thr Cys
            420                 425                 430
```

Thr Ala Thr Cys Cys Cys Ala Gly Ala Gly Gly Cys Cys Ala
        435                 440                 445

Ala Ala Gly Thr Ala Cys Ala Gly Thr Gly Ala Ala Gly Gly Thr
450                 455                 460

Gly Gly Ala Thr Ala Ala Cys Gly Cys Cys Thr Cys Cys Ala Ala
465                 470                 475                 480

Thr Cys Gly Gly Gly Thr Ala Ala Cys Thr Cys Cys Ala Gly Gly
            485                 490                 495

Ala Gly Ala Gly Thr Gly Thr Cys Cys Ala Gly Ala Cys Ala
            500                 505                 510

Gly Gly Ala Cys Ala Gly Cys Ala Ala Gly Gly Ala Cys Ala Gly Cys
        515                 520                 525

Ala Cys Cys Thr Ala Cys Ala Gly Cys Thr Cys Ala Gly Cys Ala
        530                 535                 540

Gly Cys Ala Cys Cys Thr Gly Ala Cys Gly Cys Thr Gly Ala Gly
545                 550                 555                 560

Cys Ala Ala Ala Gly Cys Ala Gly Ala Cys Thr Ala Cys Gly Ala Gly
                565                 570                 575

Ala Ala Ala Cys Ala Cys Ala Ala Ala Gly Thr Cys Thr Ala Cys Gly
                580                 585                 590

Cys Cys Thr Gly Cys Gly Ala Ala Gly Thr Cys Ala Cys Cys Cys Ala
            595                 600                 605

Thr Cys Ala Gly Gly Gly Cys Cys Thr Gly Ala Gly Cys Thr Cys Gly
            610                 615                 620

Cys Cys Cys Gly Thr Cys Ala Cys Ala Ala Gly Ala Gly Cys Thr
625                 630                 635                 640

Thr Cys Ala Ala Cys Ala Gly Gly Gly Ala Gly Ala Gly Thr Gly
                645                 650                 655

Thr

<210> SEQ ID NO 41
<211> LENGTH: 21
<212> TYPE: DNA
<213> ORGANISM: Artificial sequence
<220> FEATURE:
<223> OTHER INFORMATION: Laboratory synthesis

<400> SEQUENCE: 41
ctcagggaar tarccyttga c                                             21

<210> SEQ ID NO 42
<211> LENGTH: 21
<212> TYPE: DNA
<213> ORGANISM: Artificial sequence
<220> FEATURE:
<223> OTHER INFORMATION: Laboratory synthesis

<400> SEQUENCE: 42
tcactgccat caatcttcca c                                             21

<210> SEQ ID NO 43
<211> LENGTH: 18
<212> TYPE: DNA
<213> ORGANISM: Artificial sequence
<220> FEATURE:
<223> OTHER INFORMATION: Laboratory synthesis

<400> SEQUENCE: 43
tgtaaaacga cggccagt                                                 18

```
<210> SEQ ID NO 44
<211> LENGTH: 18
<212> TYPE: DNA
<213> ORGANISM: Artificial sequence
<220> FEATURE:
<223> OTHER INFORMATION: Laboratory synthesis

<400> SEQUENCE: 44
caggaaacag ctatgacc                                                 18

<210> SEQ ID NO 45
<211> LENGTH: 5
<212> TYPE: PRT
<213> ORGANISM: Artificial sequence
<220> FEATURE:
<223> OTHER INFORMATION: Laboratory synthesis
<220> FEATURE:
<221> NAME/KEY: MOD_RES
<222> LOCATION: (1)..(5)
<223> OTHER INFORMATION: Xaa(3)=Val, Phe, Leu; Xaa(4)=Met, Val, Trp, Leu

<400> SEQUENCE: 45

Asn Tyr Xaa Xaa His
1               5

<210> SEQ ID NO 46
<211> LENGTH: 17
<212> TYPE: PRT
<213> ORGANISM: Artificial sequence
<220> FEATURE:
<223> OTHER INFORMATION: Laboratory synthesis
<220> FEATURE:
<221> NAME/KEY: MOD_RES
<222> LOCATION: (1)..(17)
<223> OTHER INFORMATION: Xaa(10)=Asn, Lys, Cys; Xaa(12)=Asn, Ser, Ala

<400> SEQUENCE: 46

Tyr Ile Asn Pro Tyr Asn Asp Gly Thr Xaa Tyr Xaa Glu Lys Phe Lys
1               5                   10                  15

Gly

<210> SEQ ID NO 47
<211> LENGTH: 8
<212> TYPE: PRT
<213> ORGANISM: Artificial sequence
<220> FEATURE:
<223> OTHER INFORMATION: Laboratory synthesis
<220> FEATURE:
<221> NAME/KEY: MOD_RES
<222> LOCATION: (1)..(8)
<223> OTHER INFORMATION: Xaa(3)=Trp, Lys, Thr, Leu; Xaa(4)=Ser, Thr,
      Lys; Xaa(5)=Met, Phe, Gly

<400> SEQUENCE: 47

Gly Gly Xaa Phe Xaa Xaa Asp Tyr
1               5

<210> SEQ ID NO 48
<211> LENGTH: 5
<212> TYPE: PRT
<213> ORGANISM: Artificial sequence
<220> FEATURE:
<223> OTHER INFORMATION: Laboratory synthesis
<220> FEATURE:
<221> NAME/KEY: MOD_RES
<222> LOCATION: (1)..(5)
<223> OTHER INFORMATION: Xaa(3)=Glu, Gly, Thr
```

```
<400> SEQUENCE: 48

Asp Tyr Xaa Met His
1               5

<210> SEQ ID NO 49
<211> LENGTH: 17
<212> TYPE: PRT
<213> ORGANISM: Artificial sequence
<220> FEATURE:
<223> OTHER INFORMATION: Laboratory synthesis
<220> FEATURE:
<221> NAME/KEY: MOD_RES
<222> LOCATION: (1)..(17)
<223> OTHER INFORMATION: Xaa(5)=Glu, Tyr, Lys; Xaa(8)=Gly, Asn, Pro;
      Xaa(13)=Glu, Asn, Gly, Ser

<400> SEQUENCE: 49

Ala Ile Asp Pro Xaa Thr Gly Xaa Thr Ala Tyr Asn Xaa Lys Phe Lys
1               5                   10                  15

Gly

<210> SEQ ID NO 50
<211> LENGTH: 8
<212> TYPE: PRT
<213> ORGANISM: Artificial sequence
<220> FEATURE:
<223> OTHER INFORMATION: Laboratory synthesis
<220> FEATURE:
<221> NAME/KEY: MOD_RES
<222> LOCATION: (1)..(8)
<223> OTHER INFORMATION: Xaa(4)=Tyr, Lys, Leu

<400> SEQUENCE: 50

Gly Thr Pro Xaa Ala Met Asp Tyr
1               5

<210> SEQ ID NO 51
<211> LENGTH: 5
<212> TYPE: PRT
<213> ORGANISM: Artificial sequence
<220> FEATURE:
<223> OTHER INFORMATION: Laboratory synthesis
<220> FEATURE:
<221> NAME/KEY: MOD_RES
<222> LOCATION: (1)..(5)
<223> OTHER INFORMATION: Xaa(3)=Phe, Asn, Tys; Xaa(4)=Leu, Asn, Gly

<400> SEQUENCE: 51

Asn Tyr Xaa Xaa His
1               5

<210> SEQ ID NO 52
<211> LENGTH: 17
<212> TYPE: PRT
<213> ORGANISM: Artificial sequence
<220> FEATURE:
<223> OTHER INFORMATION: Laboratory synthesis
<220> FEATURE:
<221> NAME/KEY: MOD_RES
<222> LOCATION: (1)..(17)
<223> OTHER INFORMATION: Xaa(4)=Pro, Gly, Ser, Cys, Lys; Xaa(14)=Asn,
      Lys

<400> SEQUENCE: 52

Tyr Ile Asn Xaa Tyr Asn Asp Gly Thr Asn Tyr Asn Glu Xaa Phe Lys
1               5                   10                  15

Gly
```

```
<210> SEQ ID NO 53
<211> LENGTH: 10
<212> TYPE: PRT
<213> ORGANISM: Artificial sequence
<220> FEATURE:
<223> OTHER INFORMATION: Laboratory synthesis
<220> FEATURE:
<221> NAME/KEY: MOD_RES
<222> LOCATION: (1)..(10)
<223> OTHER INFORMATION: Xaa(2)=Lys, Trp, Phe; Xaa(7)=Ser, Asp, Tyr

<400> SEQUENCE: 53

Ala Xaa Gly Gly Trp Phe Xaa Met Asp Tyr
1               5                   10

<210> SEQ ID NO 54
<211> LENGTH: 16
<212> TYPE: PRT
<213> ORGANISM: Artificial sequence
<220> FEATURE:
<223> OTHER INFORMATION: Laboratory synthesis
<220> FEATURE:
<221> NAME/KEY: MOD_RES
<222> LOCATION: (1)..(16)
<223> OTHER INFORMATION: Xaa(10)=Asn, Lys, Gly; Xaa(12)=Lys, Gly, Asn;
      Xaa(16)=Glu, His, Cys, Lys

<400> SEQUENCE: 54

Arg Ser Ser Gln Ser Leu Val His Ser Xaa Gly Xaa Thr Tyr Leu Xaa
1               5                   10                  15

<210> SEQ ID NO 55
<211> LENGTH: 7
<212> TYPE: PRT
<213> ORGANISM: Artificial sequence
<220> FEATURE:
<223> OTHER INFORMATION: Laboratory synthesis
<220> FEATURE:
<221> NAME/KEY: MOD_RES
<222> LOCATION: (1)..(7)
<223> OTHER INFORMATION: Xaa(1)=Lys, Arg

<400> SEQUENCE: 55

Xaa Val Ser Asn Arg Phe Ser
1               5

<210> SEQ ID NO 56
<211> LENGTH: 8
<212> TYPE: PRT
<213> ORGANISM: Artificial sequence
<220> FEATURE:
<223> OTHER INFORMATION: Laboratory synthesis
<220> FEATURE:
<221> NAME/KEY: MOD_RES
<222> LOCATION: (1)..(8)
<223> OTHER INFORMATION: Xaa(7)=Tyr, Pro, Phe, Asp

<400> SEQUENCE: 56

Ser Gln Ser Thr His Val Xaa Thr
1               5

<210> SEQ ID NO 57
<211> LENGTH: 16
<212> TYPE: PRT
<213> ORGANISM: Artificial sequence
<220> FEATURE:
<223> OTHER INFORMATION: Laboratory synthesis
<220> FEATURE:
<221> NAME/KEY: MOD_RES
<222> LOCATION: (1)..(16)
```

```
<223> OTHER INFORMATION: Xaa(4)=Tyr, Pro, Phe, Asp; Xaa(11)=Gly, Lys,
      Asn, Ser

<400> SEQUENCE: 57

Arg Ser Ser Xaa Ser Leu Val His Ser Asn Xaa Asn Thr Tyr Leu His
1               5                   10                  15

<210> SEQ ID NO 58
<211> LENGTH: 7
<212> TYPE: PRT
<213> ORGANISM: Artificial sequence
<220> FEATURE:
<223> OTHER INFORMATION: Laboratory synthesis
<220> FEATURE:
<221> NAME/KEY: MOD_RES
<222> LOCATION: (1)..(7)
<223> OTHER INFORMATION: Xaa(5)=Arg, Gly, Ser, Lys

<400> SEQUENCE: 58

Lys Val Ser Asn Xaa Phe Ser
1               5

<210> SEQ ID NO 59
<211> LENGTH: 9
<212> TYPE: PRT
<213> ORGANISM: Artificial sequence
<220> FEATURE:
<223> OTHER INFORMATION: Laboratory synthesis
<220> FEATURE:
<221> NAME/KEY: MOD_RES
<222> LOCATION: (1)..(9)
<223> OTHER INFORMATION: Xaa(4)=Thr, Lys

<400> SEQUENCE: 59

Ser Gln Ser Xaa His Val Pro Trp Thr
1               5

<210> SEQ ID NO 60
<211> LENGTH: 16
<212> TYPE: PRT
<213> ORGANISM: Artificial sequence
<220> FEATURE:
<223> OTHER INFORMATION: Laboratory synthesis
<220> FEATURE:
<221> NAME/KEY: MOD_RES
<222> LOCATION: (1)..(16)
<223> OTHER INFORMATION: Xaa(6)=Leu, Arg; Xaa(14)=Tyr, Lys, Leu, Gly

<400> SEQUENCE: 60

Arg Ser Ser Gln Ser Xaa Val His Ser Asn Gly Lys Thr Xaa Leu Gln
1               5                   10                  15

<210> SEQ ID NO 61
<211> LENGTH: 7
<212> TYPE: PRT
<213> ORGANISM: Artificial sequence
<220> FEATURE:
<223> OTHER INFORMATION: Laboratory synthesis
<220> FEATURE:
<221> NAME/KEY: MOD_RES
<222> LOCATION: (1)..(7)
<223> OTHER INFORMATION: Xaa(2)=Val, Asn, Lys, Ser

<400> SEQUENCE: 61

Lys Xaa Ser Asn Arg Phe Ser
1               5

<210> SEQ ID NO 62
<211> LENGTH: 10
```

```
<212> TYPE: PRT
<213> ORGANISM: Artificial sequence
<220> FEATURE:
<223> OTHER INFORMATION: Laboratory synthesis
<220> FEATURE:
<221> NAME/KEY: MOD_RES
<222> LOCATION: (1)..(8)
<223> OTHER INFORMATION: Xaa(2)=Gln, Cys; Xaa(7)=Tys, Pro, Trp, Asp

<400> SEQUENCE: 62

Ser Xaa Gln Ser Thr His Val Xaa Tyr Thr
1               5                   10
```